United States Patent [19]
Meyer et al.

[11] Patent Number: 6,143,877
[45] Date of Patent: Nov. 7, 2000

[54] OLIGONUCLEOTIDES INCLUDING PYRAZOLO[3,4-D]PYRIMIDINE BASES, BOUND IN DOUBLE STRANDED NUCLEIC ACIDS

[75] Inventors: Rich B. Meyer; Alexander Gall; Igor V. Kutyavin, all of Bothell, Wash.

[73] Assignee: Epoch Pharmaceuticals, Inc., Redmond, Wash.

[21] Appl. No.: 08/848,373

[22] Filed: Apr. 30, 1997

[51] Int. Cl.[7] .......................... C07H 21/00; C07H 21/02; C07H 21/04
[52] U.S. Cl. ............................. 536/22.1; 435/6; 436/501; 536/25.3
[58] Field of Search ........................ 435/6, 810; 436/501; 536/22.1, 23.1, 24.1, 24.3–33, 25.3; 935/77, 78

[56] References Cited

U.S. PATENT DOCUMENTS

| | | | |
|---|---|---|---|
| 4,400,518 | 8/1983 | Wierenga | 548/433 |
| 4,413,132 | 11/1983 | Wierenga | 548/491 |
| 4,423,229 | 12/1983 | Wierenga | 548/421 |
| 4,424,365 | 1/1984 | Wierenga | 548/421 |
| 4,496,492 | 1/1985 | Wierenga | 260/456 |
| 4,912,227 | 3/1990 | Kelly et al. | 548/421 |
| 4,978,757 | 12/1990 | Kelly et al. | 548/421 |
| 5,177,196 | 1/1993 | Meyer, Jr. et al. | 536/22.1 |
| 5,419,966 | 5/1995 | Reed et al. | 428/406 |
| 5,422,251 | 6/1995 | Fresco | 435/91.1 |
| 5,512,667 | 4/1996 | Reed et al. | 536/24.31 |
| 5,659,022 | 8/1997 | Kutyavin et al. | 536/22.1 |

FOREIGN PATENT DOCUMENTS

| | | | |
|---|---|---|---|
| 90/03370 | 5/1990 | WIPO | C07D 239/00 |
| 96/32496 | 10/1996 | WIPO | . |
| 96/40711 | 12/1996 | WIPO | C07H 21/00 |

OTHER PUBLICATIONS

Moser et al. (1987) *Science*, 238: 645–650.
Povsic et al. (1989) *J. Amer. Chem. Soc.*, 111: 3059–3061.
Durland et al. (1991) *Biochemistry*, 30: 9246–9255.
Pilch et al. (1991) *Biochemistry*, 30: 6081–6087.
Beal et al. (1991) *Science* 251: 1360–1363.
Kutyavin et al. (1993) *J. Amer. Chem. Soc.*, 115: 9303–04.
Reynolds et al. (1986) *Antibiotics (Tokeo)*, 39:319–334.
Boger et al. (1995) *Proc. Natl. Acad. Sci. USA*, 92: 3642–3649.
Hurley et al. (1984) *Science*. 226: 843–844.
Warpehoski et al. (1988) *J. Med. Chem.*, 31: 590–603.
Warpehoski et al. (1988) *Chem. Res. Toxicol.*, 1: 315–333.
Lin et al. (1991) *Biochemistry*, 30: 3597–3602.
Reynolds et al. (1985) *Biochemistry*, 24: 6228–6237.
Hurley et al. (1990) *J. Am. Chem. Soc.*, 112: 4633–4649.
Seela et al. (1986) *Helvetica Chimica Acta*, 69: 1602–1613.
Seela et al. (1988) *Helvetica Chimica Acta*, 71: 1813–1823.
Seela et al. (1988) *Helvetica Chimica Acta*, 71: 1191–1198.
Seela et al. (1989) *Nucleic Acids Research*, 17: 901–910.
Seela et al. (1986) *Liebigs. Ann. Chem.*, 1213–1221.
Cehn et al. (1995) *Nucleic Acids Res.*, 23: 2661–2668.
Robins et al. (1982) *Can. J. Chem.*, 60: 554–557.
Robins et al. (1983) *J. Org. Chem.*, 48: 1854–1862.
Giovannangeli et al. (1992) *Nucleic Acids Res.*, 20: 4275–81.
Takasugi et al. (1991) *Proc. Natl. Acad. Sci USA*, 88: 5602–5606.
Boger et al. (1987) *J. Org. Chem.*, 52: 1521–1530.
F. Seela et al.: "96. 2'–Deoxy–B–D–Ribofuranosides of N6–Methylated 7–Deazaadenine and 8–Aza–7–deazadenine : Solid Phase Synthesis of Oligodeoxyribo–nucleotides and Properties of Self–Complementary Duplexes." Helvetica Chimica Acta., vol. 72, No. 5, Aug. 9, 1989, pp. 868–881.
Czernecki S. et al: "A Novel 2@?–Deoxynucleoside Designed for Enhanced Recognition of A.T. Base–pairs" Tetrahedron Letters, vol. 37, No. 49, Dec. 2, 1996, pp. 8857–8860.

*Primary Examiner*—Ardin H. Marschel
*Attorney, Agent, or Firm*—Klein & Szekeres, LLP

[57] ABSTRACT

A triplex forming oligonucleotide is complementary pursuant to the G/T or A/G recognition motif to a homopurine, or substantially homopurine target sequence in double stranded nucleic acids, and at least one and preferably all of the guanine bases are replaced by their pyrazolo[3,4-d] pyrimidine analog, namely by 6-amino-1H-pyrazolo[3,4-d] pyrimidin-4(5H)-one. The oliginucleotides containing the pyrazolo[3,4-d]pyrimidine analog of guanine exhibit a lesser degree of self-association, and lack the nucleophilic nitrogen atom in the 7 position of guanine. The latter feature results in a diminished extent of self-crosslinking in ODNs which also have a covalently attached cross-linking agent.

29 Claims, No Drawings

OLIGONUCLEOTIDES INCLUDING PYRAZOLO[3,4-D]PYRIMIDINE BASES, BOUND IN DOUBLE STRANDED NUCLEIC ACIDS

BACKGROUND OF THE INVENTION

1. Field of the Invention

The present invention is in the field of oligonucleotides. More particularly, the present invention is in the field of oligonucleotides which include the pyrazolo[3,4-d] pyrimidine analogs of the naturally occurring guanine and adenine bases. The oligonucleotides of the invention form triplexes with homopurine target runs in double stranded nucleic acids with increased effectiveness of binding when compared to triplex forming oligonucleotides which include the naturally occurring purine bases. The oligonucleotides of the invention can be used as sequence specific probes and in anti-gene therapy.

2. Brief Description of the Prior Art

Triplex forming oligonucleotides (ODNs) which bind to homopurine, or substantially homopurine sequences in double stranded DNA, are known in the prior art. To date three basic recognition motifs have been described for the sequence specific triplexation of ODNs to homopurine runs in double-stranded DNA. In each of the motifs the ODN resides in the major groove of the DNA duplex and hydrogen bonds to the bases of the homopurine strand. Because only two of the four DNA base pairs are recognized, the triplex forming ODNs are themselves usually composed of only two bases. The most frequently used recognition motif is based upon the formation of T-A-T and C-G-C triad wherein the third strand C residues are protonated (see Moser et al., *Science* 238: 645–650). In this motif ($C^+$/T or "pyrimidine motif") the triplex forming ODN has the same polarity as the homopurine strand of the target duplex. Because the cytosine residues on the triplex forming ODN must be protonated in order to hydrogen bond to guanine in the target, low pH facilitates the formation of these triplexes. Substituting 5-methyl cytidine (C*) for cytidine (C) can increase the stability of such triplexes at physiological pH (see Povsic et al. (1989) *J. Amer. Chem. Soc.* 111: 3059–3061).

A second recognition motif, first described for oligomeric triplexes by Hogan and co-workers, is based upon the formation of T-A-T and G-G-C triad. In this motif (G/T motif) the triplex forming ODN is antiparallel to the homopurine containing G-rich duplex strand (see Durland et al. *Biochemistry* 30: 9246–9255 (1991) ), and parallel to the homopurine duplex strand which is rich in A.

A third motif also has a third strand ODN which is antiparallel to the homopurine containing duplex stand. In this A/G motif (the "purine motif"), first described for oligomeric triplexes by Pilch et al. (1991) *Biochemistry* 30: 6081–6087, and Beal et al. (1991) *Science* 251: 1360–1363 A-A-T and G-G-C triads are formed. Triplexes based on both the G/T and A/G motifs are stable at physiologic pH.

U.S. Pat. No. 5,422,251 (Fresco) is directed to such triple stranded nucleic acids, where a homopurine or substantially homopurine run (containing approximately 10 purine bases) of a conventional Watson-Crick bonded nucleic acid duplex forms a hydrogen-bonded triplex with a third strand that has bases "corresponding" to bases of the homopurine run. The Fresco patent describes the rules of "correspondence" (which is differentiated from being "complementary" pursuant to Watson-Crick theory) in that it states that A of the homopurine run in the duplex can bind to A, U/T or I (inosine) in the third strand, and G of the homopurine run in the duplex can bind to I, G and C in the third strand. The Fresco patent also teaches that forming or utilizing triple stranded nucleic acids may be useful in diagnostic applications, control of gene expression and in control of genes in single cell and multi-cell organisms. The Fresco patent suggests that base residues which are "modified slightly (to form base analogues)" may also be incorporated in the triple-stranded nucleic acids of that patent.

Oligonucleotides which are complementary in the Watson Crick or triplex forming sense to a target sequence in single or double stranded DNA (as applicable) and also have an electrophilic cross-linking functionality designed to react with a nucleophilic site, (primarily the N-7 of guanine) have been described in publications and in international applications assigned to the same assignee as the present application (See WO 96/40711 and references cited therein, and Kutyavin et al. *J. Amer. Chem. Soc.* 115 9303–04 (1993)). These oligonucleotides exhibit sequence specific binding to the target sequence and can be used as sequence specific probes and in anti-gene therapy.

Another aspect of the pertinent background of the present invention relates to the antitumor antibiotic dextrorotatory (+) CC-1065, the structure of which is shown below.

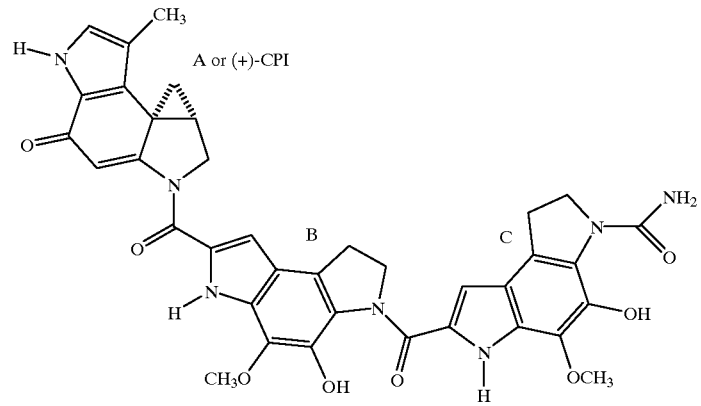

(+) CC-1065

As it can be seen, this antibiotic is composed of three repeating 1,2-dihydro-3H-pyrrolo[3,2-3-e]indole subunits. One of the subunits (CPI subunit) contains an electrophilic cyclopropyl moiety. The antibiotic is very stable in neutral aqueous solution. However, it binds strongly in the minor groove of A-T rich double stranded DNA and alkylates the DNA with resultant opening of the cyclopropyl ring. The following references describe or relate to the antibiotic CC-1065 and its CPI subunit:

Reynolds et al. (1986) J. Antibiotics (Tokyo), 39, 319–334;
Boger et al. (1995) Proc. Natl. Acad. Sci. USA, 92, 3642–3649;
Hurley et al. (1984) Science, 226, 843–844;
Warpehoski et al., (1988) J. Med. Chem., 31, 590–603;
Warpehoski et al. (1988) Chem. Res. Toxicol., 1, 315–333;
Lin et al. (1991) Biochemistry, 30, 3597–3602;
Reynolds et al. (1985) Biochemistry, 24, 6228–6237;
Hurley et al. (1990) J. Am. Chem. Soc., 112, 4633–4649.

U.S. Pat. Nos. 4,400,518; 4,413,132; 4,423,229; 4,424,365; 4,496,492; 4,912,227; and 4,978,757 describe or relate to analogs of the antibiotic CC-1065, more particularly to analogs and derivatives of the CPI subunit of this antibiotic. These analogs are said to be useful primarily as bacteriostatic or bacteriocidal agents.

A significant disadvantage or problem encountered in connection with triplex forming oligonucleotides that are designed to bind to humopurine runs in the target by the GIT or A/G motif (and therefore are rich in guanine) is the tendency of guanine rich ODNs to self-associate. Self-association of the triplex forming ODN diminishes its effectiveness to bind to the the target double stranded DNA. Moreover, the nitrogen atom in the 7 position of the guanine base in nucleotides and oligonucleotides is a reasonably strong nucleophile. Therefore, triplex forming ODNs which also include a cross-linking agent, although definitely useful, may exhibit "self-alkylation" or "self-crosslinking" to a limited extent. Elimination of the "self-crosslinking" tendency would be considered an improvement, provided that sequence specific binding affinity to the target is maintained.

In light of the foregoing, it would be desirable to provide triplex forming ODNs which sequence specifically bind to target double stranded nucleic acids without the tendency of the guanine rich ODNs to self-associate, and when provided with a crosslinking functionality, self-crosslink in solution. This is because the lack of self-association and of self-crosslinking are likely to result in greater effectiveness of binding. Those skilled in the art will readily appreciate that as long as sequence specificity is retained, these qualities are advantageous for analytical, diagnostic, gene mapping, or like "probe" purposes, as well as for application in anti-gene therapy. The present application describes triplex forming ODNs which include the pyrazolo[3,4-d]pyrimidine analog of the natural guanine base and optionally the pyrazolo[3,4-d]pyrimidine analogs of adenine base as well, and provide the above-enumerated advantages

SUMMARY OF THE INVENTION

A triplex forming oligonucleotide of the present invention is complementary pursuant to the G/T or A/G recognition motif to a homopurine, or substantially homopurine target sequence in double stranded nucleic acids. In the terminology used in U.S. Pat. No. 5,422,251 (Fresco) the triplex forming ODN of the present invention is said to "correspond" to the homopurine target sequence in the double stranded nucleic acid. The "corresponding" terminology of the Fresco patent is, however, not used in this description, because it is believed that the nature of binding of the triplex forming ODN (TFO) to the Watson-Crick bonded double strand is adequately described and is clear in the present description and claims. As a novel feature, in the ODNs of the present invention one or more, preferably several, and still more preferably all of the guanine bases are replaced by their pyrazolo[3,4-d]pyrimidine analog, namely by 6-amino-1H-pyrazolo[3,4-d]pyrimidin-4(5H)-one. Due to lack of self-association, the triplex forming oligonucleotides (TFOs) of the invention show greater effectiveness in binding to the target double stranded DNA than the corresponding ODNs containing the naturally occurring guanine bases. A cross-linking arm attached to an internal nucleotide, or to one or both terminals of the ODN of the invention may also be present, as well as tail moieties which do not interfere with triplex formation. ODNs of the invention which have a covalently linked crosslinking functionality undergo significantly less self-crosslinking, or no self-crosslinking at all, than comparable ODNs containing guanine bases. One or more adenine bases of the ODN may also be replaced by the pyrazolo[3,4-d]pyrimidine analog of adenine. Instead of the naturally occurring β-2'-deoxyribofuranosides the ODNs of the invention may optionally contain phosphorothioate linkages, methyl phosphonates, 2'-O-alkylated ribose moieties, 2'-deoxy-2'-fluororibose moieties, α-2'-deoxyribosides, 2',3'-dideoxy-3'aminoribosides or α-arabinosides.

DETAILED DESCRIPTION OF THE INVENTION

General Embodiments

Prominent features of the novel oligonucleotide of the present invention are that (1) the ODN contains a sequence which is complementary or substantially complementary pursuant to the rules of binding under the G/T or A/G motifs to a target sequence in a double stranded nucleic acid, and (2) at least one, more preferably several, and still more preferably all guanine bases of the ODN are replaced with the pyrazolo[3,4-d]pyrimidine analog of guanine. Binding of a guanine containing nucleotide unit of a triplex forming ODN to a Watson-Crick bonded GC pair in double stranded nucleic acid is schematically illustrated in Formula 1, and the triad formed in this manner is referred to as G-GC. Formula 1 depicts binding in accordance with both G/T and A/G motifs. Binding of a thymine containing nucleotide unit of a triplex forming ODN to a Watson-Crick bonded AT pair in double stranded nucleic acid is schematically illustrated in Formula 2, and the triad formed in this manner is referred to as T-AT. The binding illustrated in Formula 2 is in accordance with the G/T motif in the reverse-Hoogsteen fashion. Binding of adenine containing nucleotide unit of a triplex forming ODN to a Watson-Crick bonded AT pair in double stranded nucleic acid is schematically illustrated in Formula 3, and the triad formed in this manner, pursuant to the A/G motif, is referred to as A-AT. Formulas 1–3 thus illustrate the binding of triplex forming ODNs which contain the naturally occurring bases, to double-stranded (ds) DNA sequences, as discovered in the prior art. As is well known, the sequence in one strand of the ds DNA where the triplex formation occurs has only purine bases or subtantially only purine bases. Such a sequence is commonly called a homopurine sequence or "homopurine run".

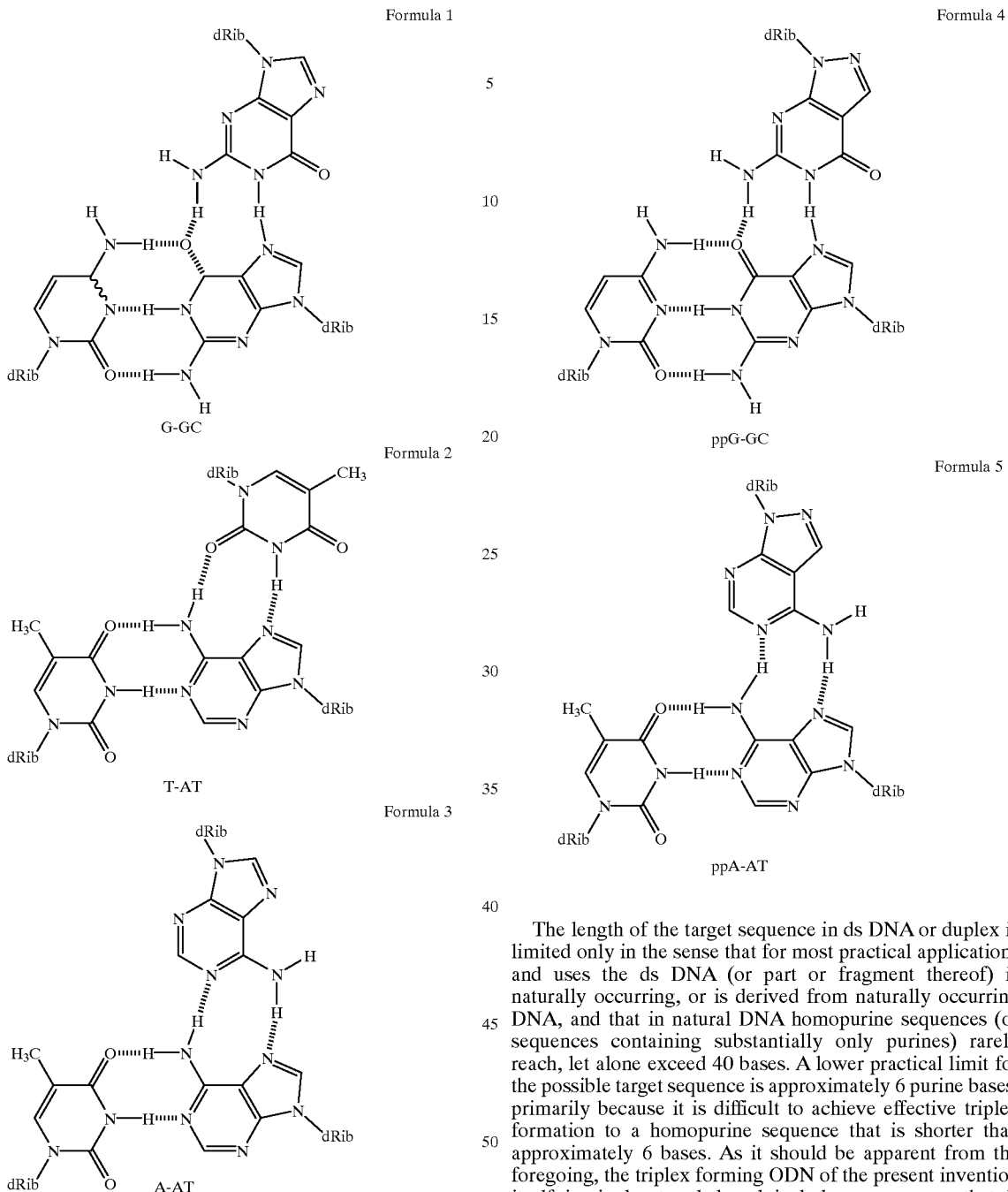

Formula 4 below illustrates binding of the pyrazolo[3,4-d]pyrimidine guanine analog (ppG) incorporated into the ODN of the present invention, to a Watson-Crick bonded GC pair in double stranded DNA. The binding illustrated in Formula 4 is in accordance with both the G/T and A/G motifs. Formula 5 illustrates binding of the pyrazolo[3,4-d] pyrimidine adenine analog (ppA) incorporated into the ODN of the present invention, to a Watson-Crick bonded AT pair in double stranded DNA. The binding illustrated in Formula 5 is in accordance with the A/G motif.

The length of the target sequence in ds DNA or duplex is limited only in the sense that for most practical applications and uses the ds DNA (or part or fragment thereof) is naturally occurring, or is derived from naturally occurring DNA, and that in natural DNA homopurine sequences (or sequences containing substantially only purines) rarely reach, let alone exceed 40 bases. A lower practical limit for the possible target sequence is approximately 6 purine bases, primarily because it is difficult to achieve effective triplex formation to a homopurine sequence that is shorter than approximately 6 bases. As it should be apparent from the foregoing, the triplex forming ODN of the present invention itself is single stranded and includes a sequence that is complemantary pursuant to the G/T and/or A/G motifs to the target sequence. After triplex formation the ODN of the invention is usually in antiparallel position to the homopurine run in target ds DNA. In addition to the sequence in the ODN which is complementary, or substantially complementary to the homopurine (or substantially homopurine) run of the target in the ds DNA, the complementary sequence of the ODN may also contain at its 3' or 5' end, or at both ends, an "overhang" comprising one or several nucleotides. A practical limit on the length of the one or two overhangs is merely that the overhangs must not interfere significantly with the triplex formation between the target sequence of the ds DNA and the complementary sequence of the ODN.

In the most preferred embodiments of the ODNs of the invention all, or substantially all guanine containing nucleotide units are replaced by the 6-amino-1H-pyrazolo[3,4-d] pyrimidin-4(5H)-one containing nucleotide (ppG). A ppG containing portion of the ODN is illustrated in Formula 6. In less preferred embodiments not necessarily all, but nevertheless several guanine containing nucleotide units are replaced by Formula 6

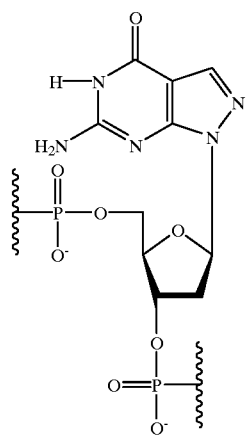

Formula 7

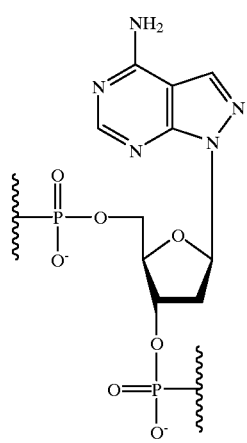

Optionally adenine containing nucleotide units of the triplex forming ODN may also be replaced by the corresponding pyrazolo[3,4-d]pyrimidine analog, to wit: by 4-amino-1H-pyrazolo[3,4-d]pyrimidine. The nucleotide unit containing this adenine analog is termed ppA, and a ppA containing portion of the ODN is illustrated in Formula 7. Thus, ODNs where at least one guanine base has been replaced with ppG and which include no ppA analog at all, as well as ODNs which in addition to ppG also have some, or possibly all adenines replaced by ppA, are within the scope of the invention.

The 2-deoxy-β-D-ribofuranosides of ppG and ppA, namely 6-amino-1-(2'-deoxy-β-D-erythro-pentofuranosyl-(1H)-pyrazolo[3,4-d]pyrimidin-4-5(H)-one and 4-amino-1-(2'-deoxy-β-D-erythro-pentofuranosyl-1H-pyrazolo[3,4-d] pyrimidine can be synthesized and the corresponding activated phosphorous containing analogs (phosphoramidites) suitable for oligonucleotide synthesis in a state-of-the-art automatic oligonucleotide synthesizer, can be obtained in accordance with the literature procedures of Seela et al. *Helvetica Chimica Acta* 69, 1602–1613 (1986), Seela et al. *Helvetica Chimica Acta* 71, 1813–1823 (1988), Seela et al. *Helvetica Chimica Acta* 71, 1191–1198 (1988) and Seela et al. *Nucleic Acids Research* 17 901–910 (1989). Each of these publications is specifically incorporated herein by reference.

As still further optional modification of the bases present in the ODNs of the invention, the pyrazolo[3,4-d]pyrimidine analog of xanthine may replace one or more of the adenine bases. The nucleotide containing the pyrazolo[3,4-d] pyrimidine analog of xanthine, (1H-pyrazolo[3,4-d] pyrimidin-4(5H)-6(7H)-dione) is designated as ppX and a ppX containing portion of the ODN is illustrated in Formula 8. ppX and the corresponding nucleosides and nucleotides can be obtained in accordance with the literature procedure of Seela et al., *Liebigs. Ann Chem.* 1986 1213–1221.

Formula 8

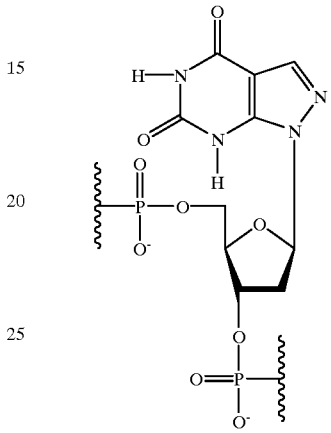

In the presently preferred embodiments of the ODNs of the invention the sugar or glycosidic moieties are 2-deoxyribofuranosides, and all internucleotide linkages are the naturally occurring phosphodiester linkages. In alternative embodiments however, instead of 2-deoxy-β-D-ribofuranose, β-D-ribofuranose may be present where the 2-OH of the ribose moiety is alkylated with a $C_{1-6}$ alkyl group (2-(O-$C_{1-6}$ alkyl) ribose) or with a $C_{2-6}$ alkenyl group (2-(O-$C_{2-6}$ alkenyl) ribose), or is replaced by a fluoro group (2-fluororibose). Alternatively, the sugar-phosphate backbone of the ODNs of the present invention may comprise α-D-arabinofuranosides, β-2'-deoxyribofuranosides or 2',3'-dideoxy-3'-aminoribofuranosides. ODNs containing α-D-arabinofuranosides can be obtained in accordance with the teachings of U.S. Pat. No. 5,177,196, the specification of which is expressly incorporated herein by reference. ODNs containing 2',3'-dideoxy-3'aminoribofuranosides can be obtained in accordance with the publication Chen et al. *Nucleic Acids Res.* 23 (14), 2661–2668 (1995), expressly incorporated herein by reference. The phosphate backbone of the ODNs of the invention may also be modified so that the ODNs contain phosphorothioate linkages and or methylphosphonates.

The ODNs of the present invention may also have intercalators, lipophilic groups, minor groove binders, reporter groups, chelating agents and cross-linking agents attached either to one or more of the internally located nucleotide bases, or to the 3' or 5' phospate end, or to both ends. The nature and attachment of intercalator, lipophilic groups, minor grove binders, reporter groups and chelating agents to oligonucleotides are presently well known in the state-of-the-art, and are described for example in U.S. Pat. Nos. 5,512,667, 5,419,966 and in the publication WO 96/32496, which are incorporated herein by reference. Cross-linking agents are a particularly important class of functional groups which can be attached to the ODNs of the invention, and therefore ODNs carrying cross-linking functionalities are described in more detail below. The ODNs of the invention may also have a relatively low molecular weight "tail moiety" attached either at the 3' or 5' end, or at both ends. By way of example a tail molecule may be a phosphate, a phosphate ester, an alkyl group, and aminoalkyl group, or a lipophilic group. The tail moiety may also link the intercalators, lipophilic groups, minor groove binders, reporter groups, chelating agents and cross-linking functionalities to the ODNs of the invention. The nature of tail moieties and methods for obtaining ODNs with various tail moieties are also described in the above-referenced U.S. Pat. Nos. 5,512,667 and 5,419,966.

With regard to the possible variations of the nucleotide units, the "phosphate backbone", "tail" and various appendages such as intercalators, lipophilic groups, minor groove binders, reporter groups, chelating agents and cross-linking functionalities of the ODNs of the present invention, the following should be kept in mind. The first and principal limitation has been described above, namely that the ODN must include a sequence that is complementary or substantially complementary pursuant to the G/T and or A/G motifs to the homopurine or substantially hompurine target sequence in ds DNA, and at least one, and preferably several guanine bases must be replaced by the ppG analog. Beyond this principal limitation, the above-mentioned structural variations and appendages must not interfere significantly with the triplex formation between the ODN and the target sequence in the ds DNA.

Embodiments Containing a Cross-linking Functionality, ODN-Crosslinker Conjugates A class of preferred embodiments of the ODNs of the present invention also include one or more cross-linking functionalities whereby after the ODN is bound to a complementary target sequence of ds DNA, the cross-linking functionality irreversibly reacts with the target and forms a covalent bond therewith. Advantages of such covalent linking to a target sequence are in analytical, diagnostic use, as in hybridization probes, and in therapeutic (anti-gene) applications. The presence of the ppG analogs instead of the guanine based nucleotides in the ODNs of the invention decrease the likelihood of self-association and the likelihood of self-crosslinking, thereby rendering the ODNs of the present invention more effective as sequence specific crosslinkers. and as such, as more effective diagnostic agents, probes and anti-gene therapeutic agents.

The following considerations are pertinent as far as the cross-linking functionalities or agents incorporated into this class of ODNs are concerned.

The cross-linking agents are covalently bonded to a site on the ODN. The length and steric orientation of the cross-linking functionality should be such that it can reach a suitable reaction site in the target ds DNA after the ODN has formed a triplex with the target. By definition, the cross-linking functionality or agent has a reactive group which will react with a reactive group in the target sequence of the ds DNA. The cross-linking agent (or agents) may be covalently attached to one or more of the heterocyclic bases, to the sugar or modified sugar residues, or to the phosphate or modified phosphate functions of the ODNs. It is presently preferred in accordance with the invention that the cross-linking agent or functionality be attached to a phosphate at one or both ends of the ODN. As explained below, this usually means attachment of the cross-linking functionality through a "tail", or to a "tail" which is attached to a terminal phosphate or modified phosphate group. Conceptually the "tail" moiety, just like the "linker arm" described below may also inculde the terminal phosphate (or modified phosphate) of the oligonucleotide.

In simple terms the cross-linking agent itself may conceptually be divided into two groups or moieties, namely the reactive group (1), which is typically and preferably an electrophilic atom or center such as an electrophilic carbon that carries a leaving group (L), the electrophilic center being attached to or being part of an "arm" (A) (2) which attaches the reactive group (1) to the respective site on the ODN.

The leaving group and/or leaving group and reactive center combination may be chosen from, for example, such groups as chloro, bromo, iodo, $SO_2R'''$, or $S+R'''R''''$, where each of $R'''$ and $R''''$ is independently $C_{1-6}$alkyl or aryl or $R'''$ and $R''''$ together form a $C_{1-6}$alkylene bridge. Chloro, bromo and iodo are preferred. Within these groups haloacetyl groups such as —$COCH_2I$, and bifunctional "nitrogen mustards", such as —N—$[(CH_2)_2—Cl]_2$ are preferred. The leaving group and reactive center combination may also be a moiety that after reaction with the target breaks a covalent bond but still remains covalently linked to the ODN and, because of the cross-linking, to the target ds DNA as well. A preferred example of the cross-linking functionality, (MCPI) described in detail below, includes a leaving group and reactive center combination that undergoes a rearrangement as a result of the crosslinking reaction. Depending on the nature of the particular leaving group and reactive center combination, the group to be used is chosen in each case to give the desired specificity of the irreversibly binding probes.

As noted above the "arm" (or linker arm) A may conceptually be regarded as a single entity which covalently bonds the ODN to the electrophilic center and may include the electrophilic center, and attaches the leaving group L, and maintains the electrophilic center and leaving group L at a desired distance and steric position relative to the ODN. Nevertheless in practice the "arm" A may be constructed in a synthetic scheme where a bifunctional molecule is covalently linked to the ODN and a moiety containing the electrophilic center and leaving group L is attached in another synthetic step or steps.

A general formula of the cross linking function is thus —A—L, or —A—$L_2$ where L is the above defined leaving group and A is a moiety that is covalently linked to the ODN. The A "arm" moiety itself should be unreactive (other than through electrophilic center and the leaving group L) under the conditions of triplex formation of the ODN with the target sequence, and should maintain the leaving group L in a desired steric position and distance from the desired site of reactions such as an N-7 position of a guanosine residue or N-3 position of a adenosine in the target sequence. In this regard one should distinguish between two major types of cross-linking agents. The reactive center and leaving group of those which after triplex formation reach through the major groove of ds DNA, should be held at an "arm's length" from the ODN which is equivalent to the length of a normal alkyl chain of approximately 2 to 20 carbons. Cross-linking agents which are also minor groove binder, or reach across the minor groove may require a much greater arm's length, equivalent to the length of a normal alkyl chain of approximately 30 to 80 atoms.

An examplary more specific formula for a class of preferred embodiments of the cross-linking function is

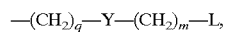

where L is the leaving group, defined above, m is 1–10 inclusive, and q is independently 1–12 inclusive, and where Y is defined as a "functional linking group". A "functional linking group" is a group that has two functionalities, for example —NH$_2$ and —OH, or —COOH and —OH, or —COOH and —NH$_2$, which are capable of linking the (CH$_2$)$_q$ and (CH$_2$)$_m$ bridges. An acetylenic terminus (HC≡C—) is also a suitable functionality for Y, because it can be coupled to certain heterocycles, as described below.

Other examplary and more specific formulas for a class of preferred embodiments of the cross-linking function are

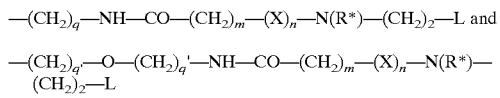

where q, m and L are defined as above in connection with the 8 description of the cross-linking functions, q' is 1 to 12 inclusive, q" is 2 9 to 10 inclusive, X is phenyl or simple substituted phenyl (such as chloro, bromo, lower alkyl or lower alkoxy substituted phenyl) or condensed phenyl (such as naphthyl or quinolinyl)), n is 0 or 1, and R* is H, lower alkyl or (CH$_2$)$_p$—L. Those skilled in the art will recognize that the structure —N(R*)—(CH$_2$)$_2$—L describes a "nitrogen mustard", which is a class of potent alkylating agents. A class of preferred cross-linking agents include the functionality —N(R*)—(CH$_2$)$_2$—L where L is halogen, preferably chlorine; and even more preferred are cross linking agents which include the grouping —N—[(CH$_2$)$_2$—L]$_2$ (a "bifunctional" N-mustard). Thus a preferred partial structure of the cross linking agent includes the grouping —CO—(CH$_2$)$_3$—C$_6$H$_4$—N—[(CH$_2$)$_2$Cl]$_2$ (chlorambucil, also abbreviated as ClAmb).

The just-noted cross-linking group is commonly known as the "chlorambucil" group or function and is utilized in a preferred embodiment which is described in the experimental section and in connection with the demonstration of the binding and alkylating ability of the ODNs of the invention. The chlorambucil function (and other cross-linking functions) can be attached to a "tail" moiety linked to a terminal phosphate of the ODN, such as an n-hexylamine bearing tail at the 5' and 3' ends of the ODN, in accordance with the following structure:

R'—O—(CH$_2$)$_6$—NH—CO—(CH$_2$)$_3$—C$_6$H$_4$—N—[(CH$_2$)$_2$Cl]$_2$ where R' signifies the terminal 5' or 3'-phosphate group of the ODN.

The foregoing generalized lengths of the linking arms (and definitions for the symbols q, m, n, and q" apply to cross-linking groups which reach across the major groove of ds DNA.

In other embodiments, the cross-linking functionality is covalently linked to a heterocyclic base, for example to the uracil moiety of a 2'-deoxyuridylic acid building block of the ODN. Such a modified uracil moiety may take the place of a thymine (T) that would otherwise be present in the triplex forming ODN pursuant to the G/T motif. The linkage can occur through the intermediacy of an amino group, that is, the "arm-electrophilic-center-leaving group combination" (A—L) may be attached to a 5-amino-2'-deoxyuridylic acid building unit of the ODN. In still other embodiments the "arm-electrophilic-center-leaving group combination" (A—L) is attached to the 5-position of the 2'-deoxyuridylic acid building unit of the ODN by a carbon-to-carbon bond. Generally speaking, 5-substituted-2'-deoxyuridines can be obtained by an adaptation of the general procedure of Robins et al. (*Can. J. Chem.,* 60:554–557 (1982); *J. Org. Chem.,* 48:1854–1862 (1983)). In accordance with this adaptation, palladium-mediated coupling of a substituted 1-alkyne to 5-iodo-2'-deoxyuridine gives an acetylene-coupled product. The acetylenic dUrd analog is reduced, with Raney nickel and hydrogen for example, to give the saturated compound, which is then used for direct conversion to a reagent for use on an automated DNA synthesizer. Examples of reagents which can be coupled to 5-iodo-2'-deoxyuridine in accordance with this method are HC≡CCH$_2$OCH$_2$CH$_2$N(CO)$_2$C$_6$H$_4$ (phtalimidoethoxypropyne) and HC≡CCH$_2$OCH$_2$CH$_2$NHCOCF$_3$ (trifluoroacetamidoethoxypropyne).

In these examples the nucleosides which are obtained in this scheme are incorporated into the desired ODN, and the alkylating portion of the cross-linking agent is attached to the terminal amino group only after removal of the respective phthalic or trifluoroacetyl blocking groups. Other examples of nucleotides where the crosslinking agent is attached to a heterocyclic base, are 2'-deoxy-4-aminopyrazolo[3,4-d]pyrimidine derivatives. These compounds can be made in accordance with the teaching of published PCT application WO: 90/03370 (published on Apr. 5, 1990). In these compounds the crosslinking arm is attached at the 3-position, which is equivalent to the 7-position of purine.

In summary, in situations where the cross-linker is attached to a heterocyclic base (as distinguished from a terminal phosphate) the crosslinking side chain (arm=A) should be of sufficient length to reach from a purine 7- or 8-position, pyrimidine 5-position, or pyrazolopyrimidine 3-position and react with the N-7 of a purine (preferably guanine) in the homopurine (or substantially only purine) run of the ds DNA. The crosslinking side chain (arm=A) holds the functional group away from the base when the base is triplexed with the ds DNA. As noted above, for crosslinkers reaching to the major groove, broadly the arm A should be equivalent in length to a normal alkyl chain of 2 to 20 carbons. Generally speaking, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and SO$_2$NR', where R'=H or C$_{1-6}$alkyl). Such functionalities, including aliphatic or aromatic amines, exhibit nucleophilic properties and are capable of serving as a point of attachment to such groups as —(CH$_2$)$_m$—L, and

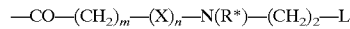

which are described above as components of examplary cross-linking functional groups. For cross-linking functionalities which reach across the minor groove a longer arm is needed. These are described in more detail below in connection with embodiments incorporating cyclopropapyrroloindole (CPI) or related reactive group as a cross-linker.

After the nucleoside or nucleotide unit which carries the crosslinking functionality A—L, or a suitable precursor thereof, (such as the —(CH$_2$)$_q$—NH$_2$ or —(CH$_2$)$_q$—Y group, where Y terminates with a nucleophilic group such as NH$_2$) is prepared, further preparation of the modified oligonucleotides of the present invention can proceed in accordance with state-of-the-art.

In addition to the above described cross-linking agents which react with a nucleophilic site on the ds DNA to bring about covalent attachment of the ODN to the target ds DNA sequence, the ODNs of the invention may also have a psoralen moiety attached through an appropriate linker arm. Oligonucleotides carrying attached psoralens are described for example in the publications by Giovannangeli et al. (1992) *Nucleic Acids Res.* 20, 4275–81; and Takasugi et al. (1991) *Proc. Natl. Acad. Sci. USA* 88, 5602–5606, which are specifically incorporated herein by reference. The above-described generic principles pertaining to the structure, synthesis and attachment of the linker arm to the ODN of the invention, as well as the state-of-the-art pertaining to cross-linking with psoralen or like moieties, enables one of ordinary skill in the art to make and use an ODN of the present invention that has a psoralen or like moiety attached for cross-linking with the target.

In light of the foregoing, a generalized structure for the ODNs of the present invention, whether or not the ODNs include the optional intercalators, lipophilic groups, minor grove binders, reporter groups, chelating agents, crosslinking agents, one or more modified sugar or phosphate groups is shown in Formula 9.

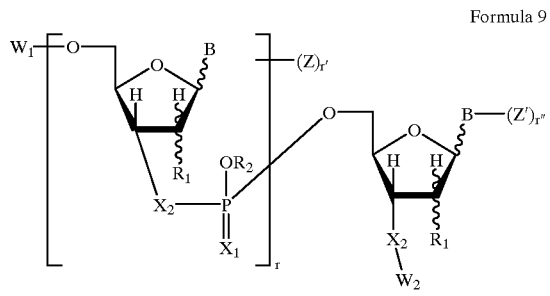

Formula 9 where
B is a heterocyclic base;
$R_1$ independently is H, $O-C_{1-6}$alkyl, $OC_{2-6}$alkenyl, or F;
$R_2$ independently is H or $C_{1-6}$alkyl, or $R_2$ represents a cation bound to the negatively charged phosphate moiety;
r is an integer between approximately 5 to approximately 79;
$X_1$ independently is O or S;
$X_2$ independently is O or NH;
r' is an integer between 0 and 5;
r" is an integer between 0 and 1;
Z and Z' each independently represent an intercalator group, a lipophilic group, a minor groove binder group, a reporter group, a chelating group, or a cross-linking group, each of said groups including a linker arm that connects the Z group and/or the Z' group respectively, to a heterocyclic base of the oligonucleotide;
  $W_1$ is H, a phosphate or thiophosphate group, a tail moiety, or $W_1$ is selected from an intercalator group, a lipophilic group, a minor groove binder group, a reporter group, a chelating group, or a cross-linking group, each of said groups including a linker arm that connects the $W_1$ group to the 5'-end of the oligonucleotide;
  $W_2$ is H, a phosphate or thiophosphate group, a tail moiety, or $W_2$ is selected from an intercalator group, a lipophilic group, a minor groove binder group, a reporter group, a chelating group, or a cross-linking group, each of said groups including a linker arm that connects the $W_1$ group to the 3'-end of the oligonucleotide, and
wherein the sequence of the nucleotide units is such that at least approximately 6 consecutive or substantially consecutive nucleotides are complementary or substantially complementary pursuant to G/T and/or A/G motif to a target sequence consisting substantially of purine bases in double stranded nucleic acid, and where at least one guanine base is replaced by the pyrazolo[3,4-d]pyrimidine analog of the guanine base.

Embodiments Containing Cyclopropapyrroloindole or Analogous Crosslinking Functionalities Another class of crosslinking agents or functionalities which are utilized in preferred embodiments of the ODN-crosslinking agent conjugates of the invention reach through the minor groove to accomplish cross-linking. Preferred examples utilize a cyclopropapyrroloindole (CPI) or related reactive group to accomplish crosslinking. Generally speaking the cyclopropapyrroloindole (CPI) or related reactive group may be attached to a heterocyclic base or to the 3' or 5' phosphate end of the ODN of the invention. In either case, generally speaking, the attachment can be accomplished through the type of linkers or linking arms (A) discussed above, where the length of the linking arm is adjusted to accomodate the length and reactivity of the cyclopropapyrroloindole (CPI) moiety itself.

Specifically, cyclopropapyrroloindole (CPI) moiety as a cross-linking function is related to the known antibiotic CC-1065 the structure of which is provided in the introductory section of this application for patent. The CPI related crosslinking functionalities used in the ODNs of the present invention can be described by the general formulas 10 and 11

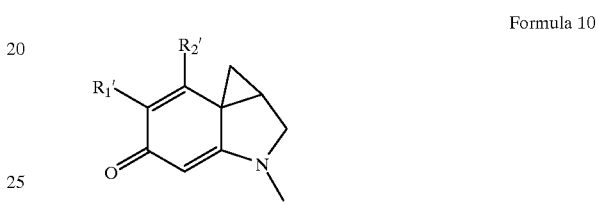

Formula 10

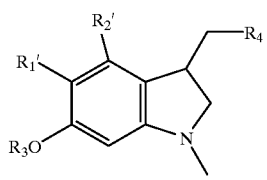

Formula 11 where the linking group or linking arm attaches the groups shown in these formulas through the nitrogen of the pyrrole ring, and where $R_1'$ and $R_2'$ independently are H, alkyl of 1 to 6 carbons, alkoxy of 1 to 6 carbons, amino, alkylamino or dialkylamino where the alkyl group has 1 to 6 carbons, phenyl, $(C_{1-6}$alkyl)phenyl, heterocyclic consisting of a 5 to 7 membered ring and including 1 to 3 heteroatoms independently selected from the group consisting of O, N and S, $(C_{1-6}$alkyl)heterocyclic, or the $R_1'$ and $R_2'$ groups jointly form a carbocyclic ring of 5 to 7 atoms or a $(C_{1-6}$alkyl) carbocyclic ring of 5 to 7 atoms, a heterocyclic or a $(C_{1-6}$alkyl)heterocyclic ring where heterocyclic is defined as above, with the proviso that $R_1'$ and $R_2'$ are not both selected from the group consisting of phenyl, $(C_{1-6}$alkyl)phenyl, heterocyclic and $(C_{1-6}$alkyl)heterocyclic.

The $R_3$ group of the "CPI-type" crosslinking agents shown in Formula 11 is preferably H or a group that cleaves under the physiological conditions of using the ODN-crossliker conjugate. In this regard the $R_3$ may be an acyl group of an alkanoic acid of 1 to 6 carbons (such as acetyl) or phosphoryl group or other group which forms a readily cleavable ester, as well a water labile trimethylsilyl or like trialkylsilyl group.

With regard to the $R_1'$ and $R_2'$ groups in Formulas 10 and 11, cross-linking functions are preferred in accordance with the present invention where $R_1'$ and $R_2'$ jointly form a carbocyclic or heterocyclic ring, even more preferably a pyrrol ring, and still more preferably a lower alkyl (such as methyl) substituted pyrrol ring, as is shown in formulas depicting the preferred embodiments.

The $R_4$ group of Formula 11 is a leaving group, such that the structure shown in Formula 11 is activated under physiological condition to form the cyclopropyl ring, or to act as an alkylating agent per se. Generally speaking, examples for the $R_4$ leaving group are the same as for the leaving group L described above. Specific examples in this instance are Cl, Br, I, $OSO_2R''$ where $R''$ is $(C_{1-6})$alkyl, phenyl, tolyl, bromophenyl, nitrophenyl, and trifluoromethyl, with the chloro group being presently preferred.

Referring still to Formulas 10 and 11 it is apparent that the CPI or CPI analog moiety incorporated into the ODN-crosslinker conjugates of the present invention exists in enantiomeric forms, similar to the (+) and (−) forms of the naturally occurring CC-1065 antibiotic. ODN-crosslinker conjugates incorporating either or both enantiomers of the CPI and analog moiety or their racemic mixture are all considered within the scope of the invention.

Preferred examples of linkers for CPI or CPI-analog cross-linking functions

In embodiments of the ODN-crosslinker conjugates of the present invention which also incorporate the CPI or analog cross-linking functionality, the CPI (or analog) group is preferably attached to one of the terminal phosphates of the ODN through linking groups or structures, the preferred examples of which are described below.

As disclosed in the general description of linking arms, the linking group for these preferred examples also, is generally a bifunctional molecule so that one functionality, such as a hydroxyl functionality, is attached for example to the phosphate on the 5' or 3' end of the ODN, and the other functionality such as a carbonyl group (CO) is attached to the ring nitrogen in the cyclopropapyrrolo group of the CPI or CPI analog moiety. Alternatively, the linking group may be derived from an amino alcohol so that the alcohol function is linked to the 3'-phosphate or 5'-phosphate end of the ODN and the amino function is linked through a carbonyl group to the above-mentioned ring nitrogen. Still another alternative example of a linking group includes an aminoalcohol (attached to the 3' or 5'-phosphate with an ester linkage) linked to a dicarboxylic acid with a peptide bond, which in turn is linked through its second carbonyl group to the ring nitrogen of the cyclopropapyrrolo group. Yet another alternative example of the linking group includes a —$CH_2$—S linkage to a phosphorothioate group at the 3' or 5' terminus of the ODN, where the methylene group is linked to the ring nitrogen through further peptide bonds. As a still further alternative example of the linking group, an alkylamine (such as a hexylamine) tail is attached to the 3'- or 5'-phosphate terminus of the ODN by a phosphate ester linkage, the amine function is connected with a dicarboxylic acid radical to tricyclic moiety, such as a subunit of the antibiotic CC-1650. The latter, in turn, is connected with a carbonyl group to the CPI or CPI analog moiety. The linking group may also include an "internal" ether (such as —$CH_2OCH_2$-) or sulfide (such as —$CH_2SCH_2$—) linkage.

Thus, preferred embodiments of the group linking the CPI (or analog) functionality to the 3' or 5' phosphate (or thiophosphate) terminus of the ODN of the invention have the formulas:

—$O(CH_2)_{m''}CO$—;

—$O(CH_2)_{m''}NHCO$—;

—$O(CH_2)_{m''}NHCO(CH_2)_nCO$—;

—$(CH_{2m''}CO$— (preferably linked to a thiophosphate terminal);

—$(CH_2)_{m''}CONH(CH_2)_{n''}CO$ (preferably linked to a thiophosphate terminal);

—$(CH_2)_{m''}CH(OH)(CH_2)_{n''}NHCO(CH_2)_{p''}HCO$—, and

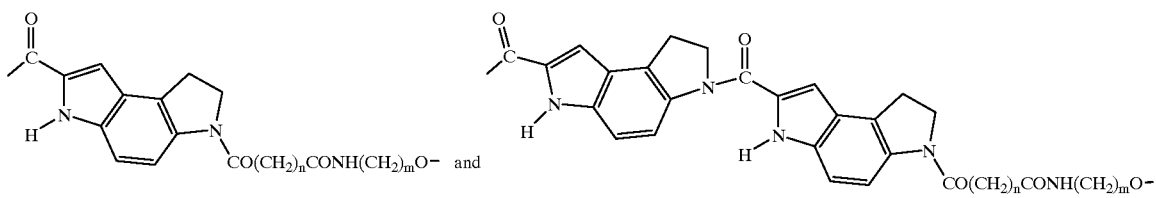

where the limitation on m", n" and p" is that the CPI or CPI analog moiety should not be separated by more than approximately 100 atoms from the ODN as counted in a direct line.

The presently most preferred embodiments of the CPI-type cross-linking function and linking arm combination attached to the 5'-end of the ODNs of the invention, are shown below in Formula 12, Formula 12

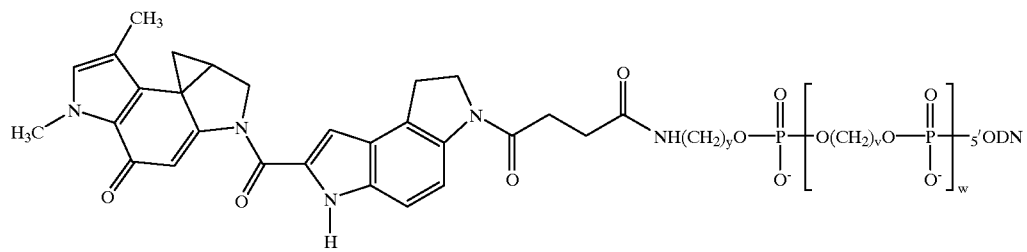

where v is an integer approximately between 1 to 6, w is an integer approximately between 3–15 and y is an integer approximately between 2 and 6. In the presently most preferred embodiment v is 3, w is 8 and y is 6.

ODN Synthesis, and Synthesis of Preferred Embodiments

Synthesis of preferred embodiment of cyclopropapyrroloindole crosslinking moiety The preferred embodiment of the cyclopropapyrroloindole crosslinking moiety was prepared starting with 5-(benzyloxy)-1,2,7,8-tetrahydro-6-methyl-3-(methylsulfonyl)-8-(methylthio)-7-oxobenzo[1,2-b:4,3-b'] dipyrrole-1-methanol Acetate (1a) which is available in accordance with the literature procedures of Warpehoski et al. *J. Med. Chem.* 1988 31, 590–603 and Boger et al. *J. Org. Chem.* 1987 52, 1521–1530. The synthesis was conducted in the steps shown in Reaction Scheme 1, with the reagents shown in the scheme. These steps are described in detail in the Specific Embodiments section of this application for patent.

The 2,3,5,6-tetrafluorophenyloxy cyclopropapyrroloindole derivative 7b, shown in Reaction Scheme 1, is reacted with the preferred embodiment of an ODN, having eight propanolphosphate linkers and aminohexyl group at the 5'-end, such as the one shown in Formula 12 where v is 3, w is 8 and y is 6. ODNs having propanolphosphate linkers and an aminohexyl tail attached at the 5'-end, can be obtained by using the reagents N-MMT-hexanolamine phosphoramidite (Glen Research) and DMT-propanol phosphoramidite (Glen Research).

ODN synthesis Generally speaking, ODN synthesis can be performed in acordance with the state-of-the-art, on commercially available automatic ODN synthesizer, using the protocols supplied by the manufacturer. Details of ODN synthesis are provided below in the Specific Embodiments section.

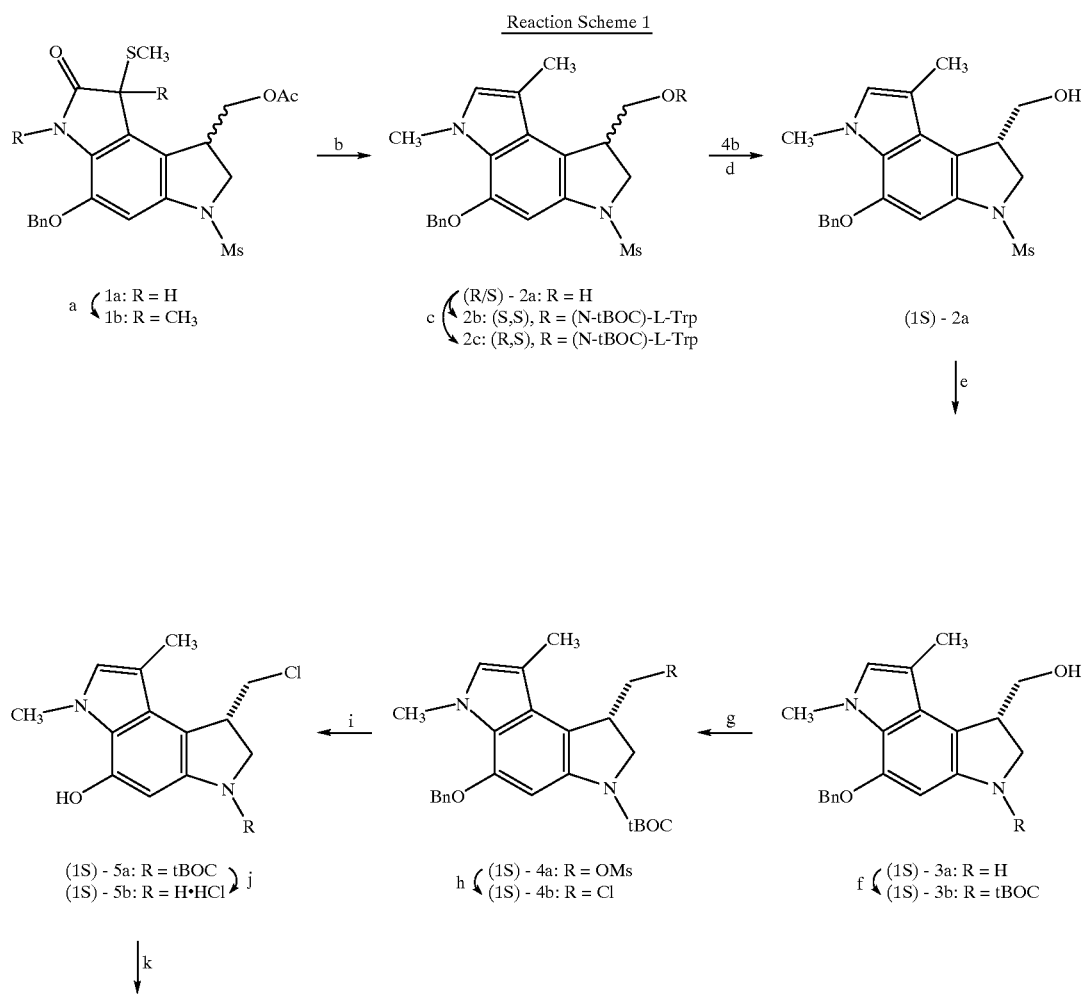

Reaction Scheme 1

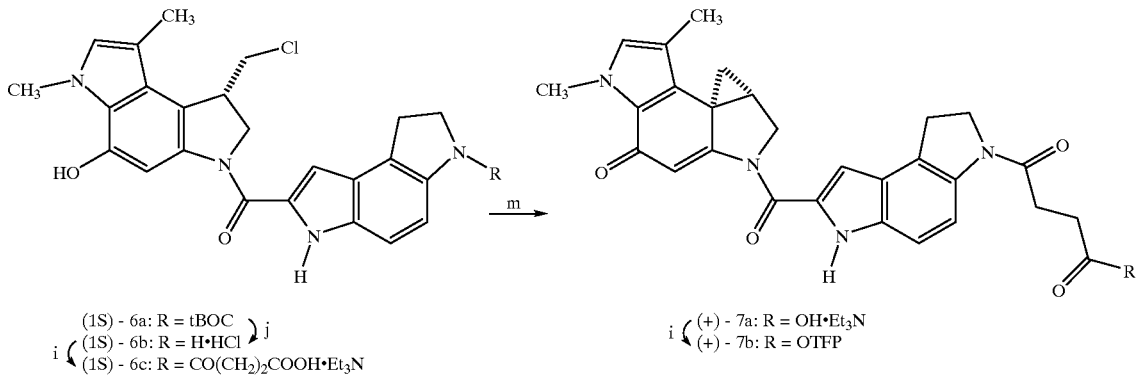

(1S) - 6a: R = tBOC  
(1S) - 6b: R = H•HCl  } j
(1S) - 6c: R = CO(CH$_2$)$_2$COOH•Et$_3$N  } i (+) - 7a: R = OH•Et$_3$N  
(+) - 7b: R = OTFP  } i

Reagents: (a) CH$_3$I, Na$_2$CO$_3$, acetone, DMF; (b) BH$_3$(CH$_3$)$_2$S, THF; (c) N-(BOC-L-tryptophan, DCC, N-methylimidazole, 1,4-dioxane; (d) NaOCH$_3$, MeOH; (e) Red-Al, THF, toluene; (f) di-tert-butyl dicarbonate, THF; (g) CH$_3$SO$_2$Cl, pyridine, CH$_2$Cl$_2$; (h) LiCl, DMF; (i) 10% Pd/C, NH$_4$COOH, THF, MeOH; (j) HCl/EtOAc; (k) 3-(tert-butyloxycarbonyl)-1,2-dihydro-3H-pyrrolo[3,2-E]indole-7-carboxylic acid, EDC, DMA; (1) succinic anhydride, Et$_3$N, (MeOH, CH$_2$Cl$_2$) or DMA; (m) Et$_3$N, CH$_3$CN, H$_2$o; (n) 2,3,5,6-tetrafluorophenyl trifluoroacetate, Et$_3$N, CH$_2$Cl$_2$ or DMA.

Demonstration of Triplex Forming and Cross-linking Ability
Binding Affinity Demonstration Ability of ODNs which include the pyrazolo[3,4-d] pyrimidine analog (ppG) of the naturally occurring guanine base containing nucleotide, to bind through triplex formation to complementary ds DNA was demonstrated in binding affinity experiments that are summarized in Table 1. In these experiments a double stranded nucleic acid (SEQUENCE ID No. 1) was incubated with a 21-mer SEQUENCE ID. No 2 that is complementary for triplex formation pursuant to the A/G motif to the homopurine run in SEQUENCE ID No. 1. The 21-mer of SEQUENCE ID No. 2 had a 5' tail and a 3' tail, but contained all natural bases. The structure of the ODN of SEQUENCE ID No. 2 is shown below aligned to SEQUENCE ID No. 1 in an antiparallel mode to illustrate the complementary and triplex forming bases.

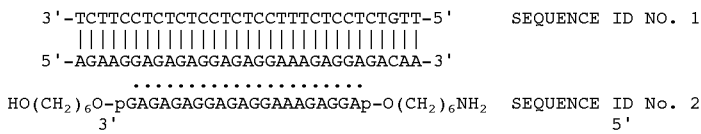

Another oligonucleotide, SEQUENCE ID No. 3, had a composition similar to SEQUENCE ID No. 2, except that all guanine containing nucleotides were replaced with the pyrazolo[3,4-d]pyrimidine (ppG) analog. The underlining of the symbol G in SEQUENCE ID No. 3 symbolizes that the underlined unit is ppG.

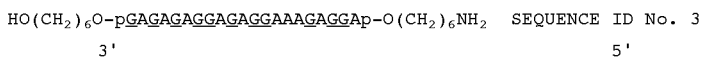

The ODN of SEQUENCE ID No. 3 was also incubated with the the double stranded nucleic acid of SEQUENCE ID No. 1. Constants of dissociation were determined by polyacrylamide gel electrophoresis (PAGE) after equilibrium conditions had been attained. The exact condition of these experiments are described in the specific embodiment/experimental section below.

TABLE 1

Constants of dissociation ($K_D$'s) for triplex formation of SEQUENCE ID No. 2 and SEQUENCE ID No. 3 with SEQUENCE ID No. 1 duplex.

| ODN | Dissociation Constant[a] | |
|---|---|---|
| | 140 mM KCl, 10 mM MgCl$_2$, 20 mM HEPES pH 7.2, 1 mM spermine | 20 mM KCl, 10 mM MgCl$_2$, 20 InM HEPES pH 7.2 |
| SEQUENCE ID No. 2 | $(18 \cdot 10^{-9})$[b] $17 \cdot 10^{-9}$ | $6.9 \cdot 10^{-9}$ |
| SEQUENCE ID NO. 3 | $7.6 \cdot 10^{-9}$ | $7.4 \cdot 10^{-9}$ |

[a]An ODN carrier, d(pA)$_8$ was added to the mixture at conc. $2 \times 10^{-7}$ M to minimize absorbtion of ODNs on the plastic tube. The use of siliconized tubes does not require carrier ODN.
[b]No carrier ODN As it can be seen from the data of TABLE 1 the ODN of SEQUENCE ID No. 3 that had all guanines replaced by the pyrazolo[3,4-d]pyrimidine analog exhibited binding under equilibrium conditions which was at least as strong, and under certain buffer conditions twice stronger than the corresponding natural (SEQUENCE ID No. 2) counterpart.

Efficiency of cross-linking demonstration

In another set of experiments two "versions" of a triplex forming ODN, one having natural guanine bases, and another having all guanines replaced by the ppG analog, and each having an identical chlorambucil carrying 5'-tail were incubated with the complementary duplex, SEQUENCE ID No. 4. The triplex forming ODN having all natural guanine bases is identified as SEQUENCE ID No. 5, and its counterpart having all ppG analogs is SEQUENCE ID No. 6. In the depiction of these ODNs "ClAmb" represents the radical $-CO-(CH_2)_3-C_6H_4-N-[CH_2-CH_2-Cl]_2$ (chlorambucil), and "p" represents $-OPO_2-O-$. In the depiction of the ODN of SEQUENCE ID No. 6 the underlining of G represents that the underlined unit is ppG.

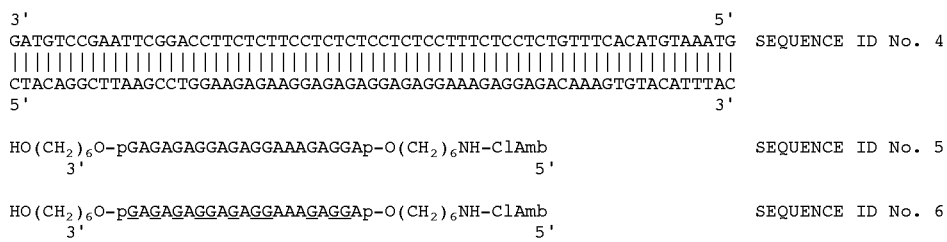

```
3'                                                                                    5'
GATGTCCGAATTCGGACCTTCTCTTCCTCTCTCCTCTCCTTTCTCCTCTGTTTCACATGTAAATG    SEQUENCE ID No. 4
||||||||||||||||||||||||||||||||||||||||||||||||||||||||||||||||
CTACAGGCTTAAGCCTGGAAGAGAAGGAGAGAGGAGAGGAAAGAGGAGACAAAGTGTACATTTAC
5'                                                                                    3'

HO(CH_2)_6O-pGAGAGAGGAGAGGAAAGAGGAp-O(CH_2)_6NH-ClAmb               SEQUENCE ID No. 5
       3'                                                 5'

HO(CH_2)_6O-pGAGAGAGGAGAGGAAAGAGGAp-O(CH_2)_6NH-ClAmb               SEQUENCE ID No. 6
       3'                                                 5'
```

After incubation at 37° C. for 21 hours the composition was analyzed by PAGE electrophoresis. Detailed conditions of the experiment are described below in the specific embodiment/experimental section. The triplex forming ODN of SEQUENCE ID No. 5 showed 45% cross-linking to the purine rich strand of the duplex of SEQUENCE ID No. 4, and 2% cross-linking to the pyrimidine rich strand. The triplex forming ODN of SEQUENCE ID No. 6 was significantly more efficient. It exhibited 79% cross-linking with the purine rich strand of the duplex SEQUENCE ID No. 4, and 7% with the pyrimidine rich strand.

Although the present inventors do not wish to be bound by theory, the greater efficiency of cross-linking by the ppG containing ODNs (SEQUENCE ID No. 6) of the invention can be explained and understood as follows. The ppG containing ODNs, under equilibrium conditions have somewhat greater affinity of binding to the complementary duplex, and have apparently more efficient rate of triplex formation than the ODNs having natural guanine bases. These two factors are influenced by the lack of or diminished self-association of the ppG containing ODNs. Moreover, the ppG containing ODNs lack the nucleophilic nitrogen (N-7) of guanine, and do not undergo self-crosslinking, or exhibit self-crosslinking to a much lesser extent than the ODNs having natural guanine bases.

Rate of cross-linking demonstration

In still another experiment (experimental details described below) the duplex of SEQUENCE ID No. 4 was incubated with a triplex forming complementary ODN of SEQUENCE ID No. 7 that contains all "natural" guanine bases, and also with the ODN of SEQUENCE ID No. 8 in which all guanine bases were replaced by the ppG analog. Both ODNs (SEQUENCE ID Nos. 7 and 8) included a 6-hydroxyhexyl "tail" at the 3' end, and a (+) MCPI-DPI cross linking agent at the 5' end. The cross-linking agent was attached via a long negatively charged linker, of the type shown in Formula 12. In fact, Formula 12 depicts the exact cross-linking agent and linker combination attached at the 5' ends, respectively, of the ODNs of SEQUENCE ID Nos. 7 and 8, in a situation where y=6, v=3 and w=8 in the formula. The entire cross-linking group and linker combination is represented by "R" in the depiction of the ODNs of SEQUENCE ID Nos. 7 and 8, and in SEQUENCE ID No. 8 "G" represents a ppG analog.

forming oligos having greater efficiency of binding, and in case of ODNs with cross-linker, greater efficiency of cross-linking, than the triplex forming ODNs of the prior art. Wheras the ODNs of the invention can be applied or administered in anti-gene therapy in numerous ways per se described in the art, ex vivo treatment of living cells taken from a patient (and subsequent administration of the treated cells to the patient) is presently contemplated as the best mode for use in anti-gene therapy. Such anti-gene therapy can result in suppessing or eliminating a gene that is not beneficial to the host, or may even result in beneficial mutation.

Specific Embodiments, Description of Experiments
Binding Affinity Experiment

Pyrimidine rich strand of the duplex SEQUENCE ID No. 1 was 5'-end $^{32}$P-labeled and mixed in buffer with two fold excess of unlabeled complementary strand. The mixture was heated for 1 minute at 95–100° C. and then incubated at 37° C. for at least 30 minutes. Final concentration of $^{32}$P-labeled

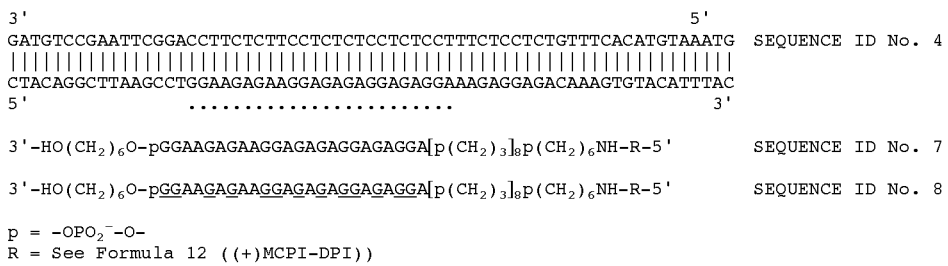

```
3'                                                               5'
GATGTCCGAATTCGGACCTTCTCTTCCTCTCCTCTCCTTTCTCCTCTGTTTCACATGTAAATG   SEQUENCE ID No. 4
|||||||||||||||||||||||||||||||||||||||||||||||||||||||||||||||
CTACAGGCTTAAGCCTGGAAGAGAAGGAGAGAGGAGAGGAAAGAGGAGACAAAGTGTACATTTAC
5'                    .......................              3'

3'-HO(CH₂)₆O-pGGAAGAGAAGGAGAGAGGAGAGGA[p(CH₂)₃]₈p(CH₂)₆NH-R-5'   SEQUENCE ID No. 7

3'-HO(CH₂)₆O-pGGAAGAGAAGGAGAGAGGAGAGGA[p(CH₂)₃]₈p(CH₂)₆NH-R-5'   SEQUENCE ID No. 8 p = -OPO₂⁻-O-
R = See Formula 12 ((+)MCPI-DPI))
```

The rate of cross-linking of the duplex (SEQUENCE ID No. 6) with each of the triplex forming ODNs, SEQUENCE ID Nos. 7 and 8, respectively, was determined by taking samples at various time intervals, and subsequent analysis by PAGE. From the resulting data the rate of alkylation was calculated and the time of 50% cross-linking (alkylation) reaction with the duplex SEQUENCE ID No. 4, was determined. The time in which 50% of the duplex was alkylated with the "natural" guanine containing ODN of SEQUENCE ID No. 7 was approximately 25 minutes. With the ODN of the invention (SEQUENCE ID No. 8) the time was approximately 9 minutes, indicating a significantly faster rate of reaction in which 50% was alkylated. When incubated for a long term (15 hours) both ODNs SEQUENCE ID. Nos. 7 and 8 cross-linked quantitatively (95%) with the target ODN Sequence ID. No. 4.

As noted above, the ODNs of the present invention can be used for diagnostic and analytical purposes, such as locating a predetermined target sequence in nucleic acids (gene-mapping and the like "probes") and in anti-gene therapy where permanent cross-linking to a gene is desired with the resulting inactivation or inducement to mutation of the gene. Description of using the triplex forming ODNs in Fresco U.S. Pat. No. 5,422,251 is of interest in this regard, as the ODNs of the present invention are suitable for the uses described in that patent, which is incorporated herein by reference. Specifically, those skilled in the art will readily understand that for diagnostic, analytical and other "probe" like applications the ODNs of the invention are to be used in substantially the same manner as triplex forming ODNs of the prior art, however with the advantages provided by the present invention, namely improved efficiency of binding. Substantially the same principle can be applied to the use of the ODNs of the invention in anti-gene therapeutic applications, where the ODNs of the invention act as triplex strand in the mixture was $2 \cdot 10^{-11}$ M; unlabeled strand was $4 \cdot 10^{-11}$ M. Concentration of triplex forming ODN SEQUENCE ID No. 2 and/or 3, respectively, added to the mixtures was in a range of $2 \cdot 10^{-5}$ to $7.2 \cdot 10^{-11}$ M. The mixtures were incubated at 37° C. for at least 15 hours and then loading solution (15% Ficoll, 0.25% Bromophenol blue, 0.25% Xylene cyanole, 5 mM MgCl$_2$) for polyacrylamide gel electorphoresis was added (10% of reaction volume).

Samples were analyzed by 8% polyacrylamide gel electrophoresis; the gel buffer contained 90 mM Tris-borate (pH 8.3), 2 mM EDTA, and 5 mM MgCl$_2$. Temperature of the gel during analysis did not exceed 11–12° C. After electrophoresis, the gel was transferred on paper, dried, and imaged using Bio-Rad molecular imager and associated computer software to measure the ratio between triplex and duplex states in each samples. Constants of dissociation were determined as equal to concentration of the respective triplex forming ODN at which the duplex/triplex ratio is 50%.

Efficiency of cross-linking experiments

Pyrimidine rich strand of the duplex SEQUENCE ID No. 4 was 5'-$^{32}$P-labeled and mixed in buffer (140 mM KCl, 10 mM MgCl$_2$, 1 mM spermine, 20 mM HEPES pH 7.2) with two fold excess of unlabeled complementary strand. The mixture was heated for 1 minute at 95° C. and then incubated at 37° C. for 30 minutes. Then the reactive triplex forming ODN, SEQUENCE ID No. 5 or 6, respectively, was added.

The final concentration of $^{32}$P-labeled strand in the mixture was $2 \cdot 10^{-7}$ M; unlabeled strand $-4 \cdot 10^{-7}$ M. Concentration of the ODN SEQUENCE ID No. 5 or 6, respectively, that was added to the mixture, was $2 \cdot 10^{-6}$ M. The mixture was incubated at 37° C. for 5 hours before analysis by denaturing gel. After electrophoresis, the gel was transferred on paper, dried and imaged using Bio-Rad molecular imager and provided computer software to measure the ratio between crosslinked product and overall radioactivity in a line.

Rate of cross-linking (kinetic) experiment

Purine rich strand of the targeted duplex SEQUENCE ID No. 4, was 5'-end $^{32}$P-labeled and mixed with two fold excess of unlabeled complementary strand, in a buffer which contained 140 mM KCl, 10 mM $MgCl_2$, 1 mM spermine, and 20 mM HEPES pH 7.2. Final concentration of $^{32}$P-labeled strand in the reaction mixture was $2 \cdot 10^{-8}$ M. The mixture had been heated at 95° C. for 1 minute and then incubated at 37° C. for at least 30 min before a reactive triplex forming ODN, SEQUENCE ID No. 7 or 8, respectively, was added to a final concentration of $2 \cdot 10^{-7}$ M. The reaction mixture was incubated at 37° C. and samples were taken in timed intervals, heated in boiling water (30 min), then in 10% aqueous piperidine (15 min), evaporated to dryness, dissolved in loading solution (8 M urea, 0.25% Bromophenol blue, 0.25% Xylene cyanole), and analyzed by denaturing polyacrylamide gel at 50–55° C. After transfer to paper and drying, the gel was radioimaged by a Bio-Rad Molecular Imager using provided computer software. Alkylation at the expected site was detected as a product of cleavage of the alkylated purine rich duplex strand which has normaly higher gel mobility due to the shorter length. Yield of reaction at each given reaction time was calculated as a ratio between radioactivity of cleavage product versus overall radioctivity in the line.

5-(Benzyloxy)-1,2,7,8-tetrahydro-6,8-dimethyl-3-(methylsulfonyl)-8-(methylthio)-7-oxobenzo [1,2-b:4,3-b'] dipyrrole-1-methanol, Acetate (1b).

To a mixture of 1a obtained in accordance with Warpehoski et al. *J. Med. Chem.* 1988 31, 590–603 (11.2 g, 23 mmol) and pulverized $K_2CO_3$ (47 g, 0.34 mol) in acetone (150 mL) and DMF (150 mL), stirred under argon was added methyl iodide (12 mL, 0.19 mol). The mixture was stirred for 24 hours and concentrated. The residue was partitioned between water and $CH_2Cl_2$. The organic phase was washed with 1 N HCl and brine, dried over $Na_2SO_4$, concentrated and chromatographed on silica gel (2% acetone in $CH_2Cl_2$). Diastereomeric product 1b was obtained as a pink amorphous solid (9.5 g, 82%): $^1$H NMR ($CDCl_3$) δ major diastereomer (~70%); 7.5–7.3 (m, 5H), 7.16 (s, 1H), 5.13 (s, 2H), 4.36 (d, 1H, J=8 Hz), 4.2–3.6 (m, 4H), 3.47 (s, 3H), 2.82 (s, 3H), 2.10 (s, 3H), 1.93 (s, 3H), 1.80 (s, 3H). Minor diastereomer (~30%); 7.5–7.3 (m, 5H), 7.18 (s, 1H), 5.14 (m, 2H), 4.95 (m, 1H), 4.2–3.6 (m, 4H), 3.47 (s, 3H), 2.81 (s, 3H), 2.09 (s, 3H), 1.92 (s, 3H), 1.73 (s, 3H). Anal. Calcd. for $C_{24}H_2N_2O_6S_2$: C, 57.13; H, 5.59; N, 5.55. Found: C, 57.17; H, 5.59; N, 5.45.

5-(Benzyloxy)-1,2-dihydro-6,8-dimethyl-3-(methylsulfonyl)benzo [1,2-b:4,3-b']dipyrrole-1-methanol (2a). Borane-methyl sulfide (2.0 M in THF, 27.5 mL, 28 mmol) was added dropwise over 15 min to the diasteriomeric mixture 1b (5.5 g, 11 mmol) in dry THF (120 mL) containing 2.5 g of 4-A molecular sieves. The solution was refluxed for 3 hours, cooled to 0° C., and quenched by careful addition of 50 mL of 1 N HCl. The mixture was stirred at 5° C. for 1 hour and then diluted with ethyl acetate. The aqueous phase was extracted with more ethyl acetate, and the combined organic phases were washed with brine, dried over $Na_2SO_4$ and concentrated. Chromatography on silica gel, eluting with 5% acetone in $CH_2Cl_2$, afforded 2a as a white solid (3.5 g, 85%):

$^1$H NMR ($CDCl_3$) δ 7.5–7.3 (m, 5H), 7.01 (s, 1H), 6.73 (s, 1H), 5.19 (s, 2H), 4.24 (d, 1H, J=10 Hz), 3.96 (s, 3H), 3.95–3.76 (m, 3H), 3.65–3.75 (m, 1H), 2.77 (s, 3H), 2.35 (s, 3H), 1.51 (t, 1H, J=6 Hz). Anal. Calcd. for $C_{21}H_{24}N_2O_4S$: C, 62.98; H, 6.04; N, 6.99. Found: C, 62.92; H, 6.06; N, 6.96.

5-(Benzyloxy)-1,2-dihydro-6,8-dimethyl-3-(methylsulfonyl)benzo [1,2-b:4,3-b']dipyrrole-1-methanol, (S)-N-2-tert-Butyloxycarbonyl-2-amino-3-(3-indolyl)propionate (2b, 2c). To a solution of racemic 2a (3.2 g, 8.5 mmol) in 20 mL of anhydrous 1,4-dioxane were added $N_a$-(tert-butyloxycarbonyl)-L-tryptophan (3.2 g, 10 mmol), N,N'-dicyclohexylcarbodiimide (2.5 g, 12 mmol) and N-methylimidazole (50 mL). The mixture was stirred overnight and then filtered to remove precipitated N,N'-dicyclohexylurea. The filtrate was evaporated to dryness to give a solid. It was washed with ether and dried in vacuo to give 5.5 g (98%) of a diastereomeric product (mixture of 2b and 2c). The diastereomers were separated by fractional crystallization from ethyl acetate/hexane: $^1$H NMR ($CDCl_3$) δ 2b (S,S-diastereomer) 8.29 (br s, 1H), 7.70–7.05 (m, 9H), 7.01 (br s, 1H), 6.96 (s, 1H), 6.72 (s, 1H), 5.17 (s, 2H), 5.09 (d, 1H, J=9 Hz), 4.68 (m, 1H), 4.31 (m, 1H), 3.94, (s, 3H), 3.81 (t, 1H, J=11 Hz), 3.63 (m, 2H), 3.28 (m, 3H), 2.69 (s, 3H), 2.34 (s, 3H), 1.45 (s, 9H); 2c (R,S-diastereomer) 8.31 (br s, 1H), 7.70–7.05 (m, 9H), 7.00 (br s, 1H), 6.94 (s, 1H), 6.71 (s, 1H), 5.16 (s 2H) with overlapping br s (1H)), 4.70 (m, 1H), 4.28 (d, 1H, J=9 Hz), 3.94, (s, 3H), 3.80–3.55 (m, 2H), 3.48 (d, 1H, J=11 Hz), 3.40–3.05 (m, 3H), 2.69 (s, 3H), 2.31 (s, 3H), 1.46 (s, 9H). Anal. Calcd. for $C_{37}H_{42}N_4O_7S$: C, 64.70; H, 6.16; N, 8.16. Found: C, 64.32; H, 6.15; N, 8.01.

(1S)-5-(Benzyloxy)-1,2-dihydro-6,8-dimethylbenzo[1,2-b:4,3-b'] dipyrrole-1-methanol ((1S)-2a). To a suspension of 2b (3.3 g, 5.0 mmol) in a mixture of methanol (50 mL) and THF (30 mL) was added 5 mL of 1 M sodium methoxide in methanol. The reaction mixture was stirred for 5 hours, becoming a clear solution in approximately 30 min. Acetic acid (0.3 mL) was added to neutralize sodium methoxide, and the solution was evaporated to dryness. The residue was partitioned between water and ethyl acetate. The organic layer was washed with brine, dried over $Na_2SO_4$ and concentrated in vacuo. Chromatography on silica gel, eluting with 5% acetone in $CH_2Cl_2$, afforded 1.6 g (85%) of (1S)-2a as a white solid. This product was shown by NMR and CHN analysis to be identical with the racemic material (2a). (1R)-2a was prepared analogously from 2c.

(1S)-5-(Benzyloxy)-1,2-dihydro-6,8-dimethyl-3-(tert-butyloxycarbonyl)benzo[1,2-b:4,3-b']dipyrrole-1-methanol ((1S)-3b). To 1.55 g (4.1 mmol) of (1S)-2a in 25 mL of dry THF were added 50 mL of toluene and 8 mL (27 mmol) of a 3.4 M solution of sodium bis(2-methoxyethoxy)aluminum hydride (Red-Al) in toluene. The clear, colorless solution was quickly heated without condenser under a flow of argon to allow THF to escape. After the internal temperature of the solution reached 85° C. (~15 min), the condenser was replaced and heating was continued for 15 min. The yellow solution was cooled, quenched by dropwise addition of 15% $K_2CO_3$ (10 mL) and diluted with ether (100 mL) and water. The yellow suspension was re-extracted with ether, and the combined pale yellow extract was washed with water, brine and dried over $Na_2SO_4$. The solution containing amine (1S)-3a was concentrated to an oil. This material was directly used in the next reaction. A solution of the crude amine in 15 mL of dry THF was treated with 1 mL (4.4 mmol) of di-tert-butyl dicarbonate; after 15 hours, the reaction mixture was concentrated in vacuo, and the residue was crystallized from 20% ethyl acetate in hexane. This afforded 1.3 g (75%) of (1S)-3b. A small portion was purified by flash chromatography in 50% ethyl acetate/hexane: mp 138–140° C. (ethyl acetate-hexane); $^1$H NMR ($CDCl_3$) δ 7.66 (br s, 1H), 7.5–7.3 (m, 5H), 6.68 (s, 1H), 5.19 (br s, 2H), 4.20 (m, 1H), 4.00 (m, 1H), 3.93 (s, 3H), 3.86 (m, 1H partially overlapping with CH$_3$ singlet), 3.8–3.6 (m, 2H), 2.37 (s, 3H), 1.57 (s, 9H). Anal. Calcd. for C$_{25}$H$_{30}$N$_2$O$_4$: C, 71.07; H, 7.16; N, 6.63. Found: C, 71.41; H, 7.36; N,6.32. A similar conversion of (1R)-2a afforded (1R)-3b.

(1S)-3-(tert-Butyloxycarbonyl)-1-chloromethyl-5-benzyloxy-6,8-dimethyl-1,2-dihydro-3H-pyrrolo[3,2-e]indole ((1S)-4b). To a solution of (1S)-3b (1.2 g, 2.8 mmol) in a mixture of dry CH$_2$Cl$_2$ (10 mL) and dry pyridine (10 mL) at 0° C. was added dropwise 1 mL (12.8 mmol) of methanesulfonyl chloride. The reaction was allowed to warm to room temperature and stand for 2 hours. It was then re-cooled to 0° C. and treated with 0.3 mL of water. After 10 min, the reaction was partitioned between CH$_2$Cl$_2$ and 5% NaHSO$_4$ (300 mL). The aqueous layer was reextracted with CH$_2$Cl$_2$. The combined organic layer was washed with 1% NaHSO$_4$ and dried over Na$_2$SO$_4$. Concentration under vacuum afforded crude mesylate (1S)-4a. To a solution of the crude mesylate in 20 mL of dry DMF was added LiCl (0.42 g, 10 mmol) and the solution was heated to 85° C. under argon and stirred at this temperature for 50 min. The reaction was cooled and partitioned between CH$_2$Cl$_2$ and water. The aqueous layer was reextracted with CH$_2$Cl$_2$. The combined organic layer was washed with water, brine and dried over Na$_2$SO$_4$. The crude product was chromatographed on silica gel, eluting with 20% ethyl acetate in hexane. Solid obtained after evaporation of the desired fractions was washed with methanol. Drying in vacuo afforded (1S)-4b (0.98 g, 79%) as a white solid: mp 155–156° C.; $^1$H NMR (CDCl$_3$) δ 7.61 (br s, 1H), 7.5–7.3 (m, 5H), 6.69 (s, 1H), 5.18 (br s, 2H), 4.25 (m, 1H), 4.00 (m, 1H), 3.92 (s, 3H), 3.7–3.9 (m, 2H), 3.36 (t, 1H, J=11 Hz), 2.37 (s, 3H), 1.59 (s, 9H). Anal. Calcd. for C$_{25}$H$_{29}$N$_2$O$_3$Cl: C, 68.05; H, 6.63; N. 6.35. Found: C, 68.09; H, 6.58; N, 6.28. Analogously, (1R)-3b was converted into (1R)-4b.

(1S)-3-(tert-Butyloxycarbonyl)1-chloromethyl-6,8-dimethyl-1,2-dihydro-3H-pyrrolo[3,2-e]indol-5-ol ((1S)-5a). To 0.89 g (2.0 mmol) of (1S)-4b in 20 mL of THF and 20 mL of methanol was added 200 mg of 10% palladium on carbon and 1.3 g (20.6 mmol) of ammonium formate. The mixture was stirred at room temperature for 20 min. The reaction mixture was then filtered and the solid collected was washed with methanol. The combined filtrates were evaporated and the residue was partitioned between water and ethyl acetate. The organic layer was washed with water, brine and dried over Na$_2$SO$_4$. Evaporation of the solvent followed by crystallization from ethyl acetate/hexane afforded (1S)-5a as a white crystalline solid (0.65 g, 93%): $^1$H NMR (CDCl$_3$) δ 7.41 (br s, 1H), 6.71 (s, 1H), 6.01 (br s, 1H), 4.23 (m, 1H), 3.97 (s (3H)+overlapping m (1H)), 3.7–3.9 (m, 2H), 3.34 (t, 1H, J=11 Hz), 2.36 (s, 3H), 1.58 (s, 9H). Anal. Calcd. for C$_{18}$H$_{23}$N$_2$O$_3$Cl: C, 61.62; H, 3 6.61; N, 7.98. Found: C, 61.61; H, 6.61; N, 7.91. (1R)-5a was prepared 4 analogously from (1R)-4b.

(1S)-1-chloromethyl-6,8-dimethyl-1,2-dihydro-3H-pyrrolo[3,2-e]indol-5-ol ((1S)-5b). 3-(tert-Butyloxycarbonyl)-1-chloromethyl-1,2-dihydro-3H-6,8-dimethylpyrrolo[3,2-e]indol-5-ol ((1S)-5a) (100 mg, 0.28 mmol) was dissolved in 5 mL of ethyl acetate saturated with HCl. A precipitate of the hydrochloride (1S)-5b started to form in 3 min. The mixture was stirred for another 30 min, then concentrated on a rotary evaporator. Residual HCl was removed by co-evaporation with dichloromethane (2×10 mL). The resulting hydrochloride (1S)-5b, a pale pink solid was immediately used in a coupling reaction. The enantiomer (1R)-5b was prepared analogously.

(1S)-6a. To a solution of freshly prepared (1S)-5b (0.33 mmol) in 5 mL of dry DMA were added 3-(tert-butyloxycarbonyl)-1,2-dihydro-3H-pyrrolo[3,2-e]indole-7-carboxylic acid (100 mg, 0.33 mmol, available from the chemical literature, (Boger et al. J. Org. Chem. 1987 52, 1521–1530) and EDC (120 mg, 0.63 mmol). After stirring for 5 hours, the mixture was cooled in ice and water (15 mL) was added. The resulting solid was collected by filtration, washed with 1 M potassium phosphate, water and dried in vacuo affording (1S)-6a as a green-yellow solid (161 mg, 91%). This was 95% pure by reverse phase HPLC. An analytical sample was purified by flash chromatography (5% MeOH in CH$_2$Cl$_2$):

$^1$H NMR (DMSO-d$_6$) δ 11.62 (s, 1H), 9.79 (s, 1H), 7.8 (br s, 1H), 7.61 (br s, 1H), 7.31 (d, 1H, J=9 Hz), 6.96 (br s, 2H), 4.63 (t, 1H, J=10 Hz), 4.50 (d, 1H, J=11 Hz), 4.1–3.8 (m with overlapping singlet (CH$_3$) at 3.92 ppm, 6H), 3.55 (t, 1H, 10 Hz), 3.4–3.1 (m, 3H overlapping with the water peak), 2.31 (s, 3H), 1.51 (s, 9H). Anal. Calcd. for C$_{29}$H$_{31}$N$_4$O$_4$Cl: C, 65.10; H, 5.84; N, 10.47. Found: C, 64.86; H, 5.94; N, 10.26. (1R)-6a was prepared analogously from (1R)-5b.

(8aS)-7b. (1S)-6a (150 mg, 0.28 mmol) was suspended in 5 mL of ethyl acetate saturated with HCl. The suspension was stirred for 40 min and concentrated in vacuo. Residual HCl was removed by co-evaporation with CH$_2$Cl$_2$ (2×10 mL). The resulting orange solid ((1S)-6b) was dissolved in 1 mL of dry DMA. Succinic anhydride (30 mg, 0.3 mmol) and triethylamine (50 mL, 0.36 mmol) were added to produce succinate (1S)-6c. After being stirred for 3 hours, the reaction mixture was diluted with acetonitrile (10 mL) followed by the addition of triethylamine (3 mL) and water (3 mL) to cause cyclization. After 1 hour, the volatiles were removed in vacuo and to the residue (DMA~1 mL) was added ether (20 mL) to precipitate the product (8aS)-7a. It was collected by filtration and dried in vacuo to give the succinate as a grey-yellow solid. To a suspension of (8aS)-7a in 3 mL of DMA were added triethylamine (200 mL, 1.44 mmol) and 2,3,5,6-tetrafluorophenyl trifluoroacetate (140 mL, 0.8 mmol). After being stirred for 1 hour, the reaction mixture was added dropwise to 10 mL of 0.3 M potassium phosphate buffer (pH 7.5), the resulting precipitate was collected by filtration, washed with water (15 mL) and ether (5 mL). Drying in vacuo afforded (8aS)-7b as a yellow-green solid (138 mg, 72%): $^1$H NMR (DMSO-d$_6$) δ 11.81 (s, 1H), 8.21 (d, 1H, J=9 Hz), 7.94 (m, 1H), 7.31 (d, 1H, J=9 Hz), 7.08 (s, 1H), 6.88 (s, 1H), 6.65 (s, 1H), 4.6–4.4 (m, 2H), 4.24 (t, 2H, J=8 Hz), 3.87 (s, 3H), 3.3 (m, 2H, overlapping with water), 3.18 (m, 1H), 3.06 (m, 2H), 2.91 (m, 2H), 1.97 (s, 3H), 1.92 (m, 1H, overlapping with CH$_3$), 1.38 (m, 1H). Anal. Calcd. for C$_{34}$H$_{26}$N$_4$O$_5$F$_4$, 2H$_2$O: C, 59.82; H, 4.43; N, 8.21. Found: C, 59.80; H, 4.04; N, 8.07. (8aR)-7b was prepared analogously from (1R)-6a.

Preparation of ODNs with pyrazolopyrimidine bases and oligo(propanol phosphate) linkers.

ODNs with eight propanolphosphate linkers and aminohexyl group at the 5'-end were prepared using N-MMT-hexanolamine phosphoramidite (Glen Research) and DMT-propanol phosphoramidite (Glen Research). Where the pyrazolopyrimidine analog of guanine was substituted, the appropriate phosphoramidite (1-[2'-deoxy-5'—O—(4,4'-dimethoxytrityl)-was synthesized according to described procedure (Seela et al. 1989 Nucleic Acids Res. 17, 901–10, and Seela et al. 1988, Helv Chim Acta, 71, 1813–1823 ). The synthesis, HPLC purification, detritylation and butanol precipitation of ODNs were carried out using standard procedures as previously described (Gamper, et al, 1993) *Nucleic Acids Res.* 21, 145–150, incorporated herein by reference. Drying of the ODN solutoins was performed under vacuum using a centrifugal evaporator.

Synthesis of N-methyl-CPI-DPI Modified ODN (SEQUENCE ID No. 7):

Hexylamine modified ODN that gave rise to SEQUENCE ID No. 7, was synthesized and purified by reverse phase HPLC using standard procedures. After detritylation, the dried ODN was taken up in 0.5 mL of water and re-purified by reversed phase HPLC on a Hamilton PRP-1 column (305×7.0 mm) using a linear gradient of 0%–100% acetonitrile in 0.05 M tributylammonium bicarbonate (pH 7) over 20 min (flow rate=2 mL/min). The desired fraction was taken to dryness on a Savant SpeedVac and reconstituted in 0.5 mL of water. The concentration was determined from the UV absorbance at 260 nm. A 250 $\mu$L aliquot of this stock solution (1.85 mg, 203 nmol) was taken to dryness in a 1.7 mL Eppendorf tube, then dissolved in 250 $\mu$L of dry DMSO (Aldrich). 14 $\mu$L of ethyldiisopropylamine and 33 $\mu$L (0.66 mg, 1.0 $\mu$mol) of a 20 mg/mL solution of (+) N-Methyl-CPI-DPI TFP ester (7b) in DMSO were added. The mixture was shaken until homogeneous and kept at ambient temperature for 16 h. The crude ODN conjugate was precipitated by adding the solution to 10 mL of 2% sodium perchlorate in acetone. After centrifugation, the supernatant was removed and the pellet was sonicated for 5 min with 2 mL of acetone. After re-centrifugation, the pellet was dried for 1 h on a SpeedVac, dissolved in 0.25 mL of water, and purified by HPLC on a Rainin Dynamax C18 column (240 x 4.6 mm) using a linear gradient of 5%-45% acetonitrile in 0.1 M triethylammonium acetate (pH 7) over 20 min (flow rate=1 mL/min). The desired fraction (16.4 min retention time) was collected and the product was precipitated by adding 100 $\mu$L of 3M sodium acetate and 4 mL of ethanol. After centrifugation, the supernatant was removed and the pellet was sonicated for 5 min with 1 mL of ethanol.

After re-centrifugation, the pellet was dried for 1 h on a SpeedVac.

The white solid product was dissolved in 0.5 mL of 10 mM HEPES buffer (pH 7.2) and analyzed for concentration by $A_{260}$ and for purity by C18 HPLC: concentration=0.88 mg/mL (0.44 mg, 24% yield), purity=100%.

Synthesis of N-methyl-CPI-DPI Modified ODN (SEQUENCE ID No. 8, pyrazolopyrimidine G analog): The procedure described above was repeated with the following changes. The same hexylamine modified ODN used above, but containing pyrazolopyrimidine G in place of each guanine was used. 0.73 mg of the TBA salt of this ODN was used for conjugation to (+) N-Methyl-CPI-DPI (7b). After HPLC purification, the white solid product was dissolved in 0.25 mL of 10 mM HEPES buffer and analyzed for concentration by A260 and for purity by C18 HPLC: concentration=0.45 mg/mL (0.11 mg, 15% yield), purity= 100%.

Synthesis of Chlorambucil Conjugated ODNs (SEQUENCE ID Nos. 5 and 6)

Hexylamine modified ODNs, which contained guanine, or the pyrazolopyrimidine analog bases (ppG), respectively were synthesized as described above, with a 5'-hexylamine tail. For conjugation, ODN (from a 2 $\mu$mole scale synthesis) was converted to the triethylammonium (TEA) salt, which was dried overnight. For conjugation to chlorabucil, an aliquot containing 1 mg of ODN was dried and dissolved in 0.2 mL of anhydrous DMSO. After addition of 10 /$\mu$L of ethyldiisopropylamine and 75 $\mu$L of a 20 mg/mL solution of chlorambucil 2,3,5,6-tetrafluorophenyl ester in DMSO (1.5 mg, prepared by treatment of chlorambucil with tetrafluorophenyl trifluoroacetate), the solution was shaken for 3 hours, then poured into 10 mL of 2% sodium perchlorate in acetone. After immediate centrifugation at 3000 0 g for 5 minutes, the pellet was vortexed with 2 mL of acetone and re-centrifuged. The washed pellet was dried for 10 minutes on a centrifugal evaporator and stored at –80° C.

This crude chlorambucil-ODN was dissolved in 0.25 mL of water and purified by C18 HPLC (5–85% acetonitrile in 0.1M TEA acetate, 40 minutes at 1 mL/min, ~20 min retention). The product was immediately precipitated with 100 $\mu$L of 3M sodium acetate and 4 mL of butanol for each mL of eluent collected. The precipitate was pelleted without delay (3000 g for 5 min), washed with 2 mL ethanol, and re-pelleted. This pellet was dried for 10 min on a centrifugal evaporator. Conjugates were stored at –80° C., where they were stable for weeks.

Chlorambucil itself is commercially available. A synthetic procedure for making chlorambucil 2,3,5,6-tetrafluorophenyl ester is given below. 2,3,5,6-Tetrafluorophenyl trifluoroacetate. A mixture of 2,3,5,6-tetrafluorophenol (55.2 g, 0.33 mol), trifluoroacetic anhydride (60 mL, 0.42 mol) and boron trifluoride etherate (0.5 mL) was refluxed for 16 hr. Trifluoroacetic anhydride and trifluoroacetic acid were removed by distillation at atmospheric pressure. The trifluoroacetic anhydride fraction (bp 40° C.) was returned to the reaction mixture along with 0.5 mL of boron trifluoride etherate, and the mixture was refluxed for 24 hr. This process was repeated two times to ensure complete reaction. After distillation at atmospheric pressure, the desired product was collected at 62° C./45 mm (45° C/18 mm) as a colorless liquid: yield=81.3 g (93%); d=1.52 g/mL; $n_D^{21}$=1.3747; IR (CHCl$_3$) 3010, 1815, 1525, 1485, 1235, 1180, 1110, and 955 cm$^{-1}$. Anal. Calcd for $C_8HF_7O_2$: C, 36.66; H, 0.38; F, 50.74. Found: C, 36.31; H, 0.43; F, 50.95.

2,3,5,6-Tetrafluorophenyl-4'-[bis(2-chloroethyl)amino] phenylbutyrate (Chlorambucil 2,3,5,6-tetrafluorophenyl ester) To a solution of 0.25 g (0.82 mmol) of chlorambucil (supplied by Fluka A. G.) and 0.3 g (1.1 mmol) of 2,3,5,6-tetrafluorophenyl trifluoroacetate in 5 ml of dry dichloromethane was added 0.2 Ml of dry triethylamine. The mixture was stirred under argon at room temperature for 0.5 h and evaporated. The residual oil was purified by column chromatography on silica gel with hexane-chloroform (2:1) as the eluting solvent to give the ester as an oil: 0.28 g (75%); TLC on silica gel (CHCl$_3$) $R_f$ 0.6; IR (in CHCl$_3$) 3010, 1780, 1613, 1521, 1485 cm$^{-1}$.

What is claimed is:

1. A method of forming a triplex from a duplex nucleic acid having in one strand thereof a target sequence that consists essentially of nucleotides of purine bases and from an oligonucleotide that includes a substantially continuous sequence of at least 6 nucleotides, which sequence is complementary in the triplex forming sense pursuant to the G/T or A/G recognition motif to the target sequence in the duplex nucleic acid, at least one guanine base containing nucleotide in the substantially continuous sequence of the oligonucleotide being replaced by the nucleotide of 6-amino-1H-pyrazolo[3,4-d]pyrimidin-4(5H)-one, the process comprising the step of:

contacting the oligonucleotide with the duplex nucleic acid.

2. A method in accordance with claim 1 wherein substantially all guanine base containing nucleotides of the substantially continuous sequence are replaced by the nucleotide of 6-amino-1H-pyrazolo[3,4-d]pyrimidin-4(5H)-one.

3. A triplex comprising:

an oligonucleotide that includes a substantially continuous sequence of at least 6 nucleotides, which sequence is complementary in the triplex forming sense pursuant to the G/T or A/G recognition motif to a target sequence in duplex nucleic acid, at least one guanine base containing nucleotide in the substantially continuous sequence of the triplex forming oligonucleotide being replaced by the nucleotide of 6-amino-1H-pyrazolo[3,4-d]pyrimidin-4(5H)-one, said triplex forming oligonucleotide further comprising at least one cross-linking agent covalently attached to the oligonucleotide, and said duplex nucleic acid including the target sequence.

4. A triplex comprising:

an oligonucleotide that includes a substantially continuous sequence of at least 6 nucleotides, which sequence is complementary in the triplex forming sense pursuant to the G/T or A/G recognition motif to a target sequence in duplex nucleic acid, at least one guanine base containing nucleotide in the substantially continuous sequence of the triplex forming oligonucleotide being replaced by the nucleotide of 6-amino-1H-pyrazolo[3,4-d]pyrimidin-4(5H)-one, and further wherein at least one adenine base containing nucleotide in the substantially continuous sequence of the triplex forming oligonucleotide is replaced by the nucleotide of 4-amino-1H-pyrazolo[3,4-d]pyrimidine or by the nucleotide of 1H-pyrazolo[3,4-d]pyrimidin-4(5H)-6(7H)-dione, and said duplex nucleic acid including the target sequence.

5. A triplex comprising a triplex forming oligonucleotide that is not a homopolymer and that includes a substantially continuous sequence of at least 6 nucleotides, which sequence is complementary in the triplex forming sense pursuant to the G/T or A/G recognition motif to a target sequence in duplex nucleic acid, at least one guanine base containing nucleotide in the substantially continuous sequence of the triplex forming oligonucleotide being replaced by the nucleotide of 6-amino-1H-pyrazolo[3,4-d]pyrimidin-4(5H)-one, the oligonucleotide having the formula

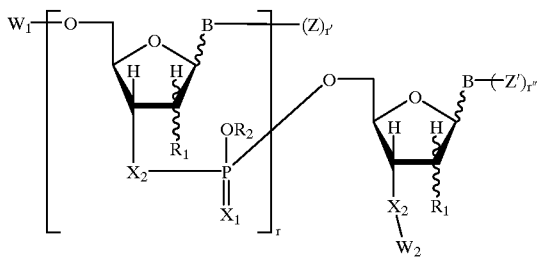

wherein

B is an independently selected heterocyclic base at least one of which is said 6-amino-1H-pyrazolo[3,4-d]pyrimidin-4(5H)-one;

$R_1$ independently is H, O-$C_{1-6}$alkyl, O$C_{2-6}$alkenyl, or F;

$R_2$ independently is H or $C_{1-6}$alkyl;

r is an integer between approximately 5 to approximately 79;

$X_1$ is independently O or S;

$X_2$ is independently O or NH;

r' is an integer between 0 and 5;

r" is an integer between 0 and 1;

Z and Z' each independently represent an intercalator group, a lipophilic group, a minor groove binder group, a reporter group, a chelating group, or a cross-linking group, each of said groups including a linker arm that connects the Z group and/or the Z' group respectively, to a heterocyclic base of the oligonucleotide;

$W_1$ is H, a phosphate or thiophosphate group, a tail moiety, or $W_1$ is selected from an intercalator group, a lipophilic group, a minor groove binder group, a reporter group, a chelating group, or a cross-linking group, each of said groups including a linker arm that connects the $W_1$ group to the 5'-end of the oligonucleotide;

$W_2$ is H, a phosphate or thiophosphate group, a tail moiety, or $W_2$ is selected from an intercalator group, a lipophilic group, a minor groove binder group, a reporter group, a chelating group, or a cross-linking group, each of said groups including a linker arm that connects the $W_1$ group to the 3'-end of the oligonucleotide, where at least one of said B groups represents a 6-amino-1H-pyrazolo[3,4-d]pyrimidin-4(5H)-one-1-yl radical, and said duplex nucleic acid including the target sequence.

6. A triplex in accordance with claim 5, wherein substantially all guanine base containing nucleotides of the substantially continuous sequence of the oligonucleotide are replaced by the nucleotide of 6-amino-1H-pyrazolo[3,4-d]pyrimidin-4(5H)-one.

7. A triplex in accordance with claim 6, wherein all guanine base containing nucleotides of the substantially continuous sequence of the oligonucleotide are replaced by the nucleotide of 6-amino-1H-pyrazolo[3,4-d]pyrimidin-4(5H)-one.

8. A triplex in accordance with claim 5, wherein at least one adenine base containing nucleotide in the substantially continuous sequence of the triplex forming oligonucleotide is replaced by the nucleotide of 4-amino-1H-pyrazolo[3,4-d]pyrimidine or by the nucleotide of 1H-pyrazolo[3,4-d]pyrimidin-4(5H)-6(7H)-dione.

9. A triplex in accordance with claim 6 where the glycosidic linkages between the heterocyclic bases B and the sugar moieties are of the β configuration.

10. A triplex in accordance with claim 9 where the $R_1$ group is H.

11. A triplex in accordance with claim 10 where $R_2$ is H or represents a cation.

12. A triplex in accordance with claim 6 where $X_2$ is O.

13. A triplex in accordance with claim 6 where at least one independently selected nucleotide of the oligonucleotide includes a Z that represents a cross-linking group.

14. A triplex in accordance with claim 6 where Z' represents a cross-linking group and r" is 1.

15. A triplex in accordance with claim 6 where $W_1$ represents a cross-linking group.

16. A triplex in accordance with claim 6 where $W_2$ represents a cross-linking group.

17. A triplex comprising a triplex forming oligonucleotide that is not a homopolymer and that includes a substantially continuous sequence of at least 6 nucleotides, which sequence is complementary in the triplex forming sense pursuant to the G/T or A/G recognition motif to a target sequence in duplex nucleic acid, at least one guanine base containing nucleotide in the substantially continuous sequence of the triplex forming oligonucleotide being replaced by the nucleotide of 6-amino-1H-pyrazolo[3,4-d]pyrimidin-4(5H)-one, the oligonucleotide having the formula

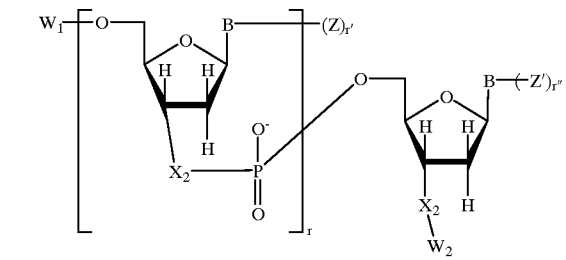

wherein

B is an independently selected heterocyclic base at least one of which is said 6-amino-1H-pyrazolo[3,4-d]pyrimidin-4(5H)-one;

$X_2$ independently is O or NH;

r is an integer between approximately 5 to approximately 79;

r' is an integer between 0 and 5;

r" is an integer between 0 and 1;

Z and Z' each independently represent an intercalator group, a lipophilic group, a minor groove binder group, a reporter group, a chelating group, or a cross-linking group, each of said groups including a linker arm that connects the Z group and/or the Z' group respectively, to a heterocyclic base of the oligonucleotide;

$W_1$ is H, a phosphate or thiophosphate group, a tail moiety, or $W_1$ is selected from an intercalator group, a lipophilic group, a minor groove binder group, a reporter group, a chelating group, or a cross-linking group, each of said groups including a linker arm that connects the $W_1$ group to the 5'-end of the oligonucleotide;

$W_2$ is H, a phosphate or thiophosphate group, a tail moiety, or $W_2$ is selected from an intercalator group, a lipophilic group, a minor groove binder group, a reporter group, a chelating group, or a cross-linking group, each of said groups including a linker arm that connects the $W_1$ group to the 3'-end of the oligonucleotide, where at least one of said B groups represents a 6-amino-1H-pyrazolo[3,4-d]pyrimidin-4(5H)-one-1-yl radical, and said duplex nucleic acid including the target sequence.

18. A triplex in accordance with claim 17 wherein substantially all guanine base containing nucleotides of the substantially continuous sequence of the oligonucleotide are replaced by the nucleotide of 6-amino-1H-pyrazolo[3,4-d]pyrimidin-4(5H)-one.

19. A triplex in accordance with claim 18 where at least one independently selected nucleotide of the oligonucleotide includes a Z that represents a cross-linking group.

20. A triplex in accordance with claim 18 Z' represents a cross-linking group and r" is 1.

21. A triplex in accordance with claim 18 where $W_2$ represents a cross-linking group.

22. A triplex in accordance with claim 18 where $W_1$ represents a cross-linking group.

23. A triplex in accordance with claim 22 where $W_1$ includes the radical $—CO—(CH_2)_3—C_6H_4—N—[(CH_2)_2Cl]_2$.

24. A triplex in accordance with claim 23 where $W_1$ represents $—PO(OH)—(CH_2)_6—NH—CO—(CH_2)_3—C_6H_4—N—[(CH_2)_2Cl]_2$.

25. A triplex in accordance with claim 22 where $W_1$ includes the N-methylcyclopropapyrroloindole radical.

26. A triplex in accordance with claim 25 where $W_1$ represents the radical

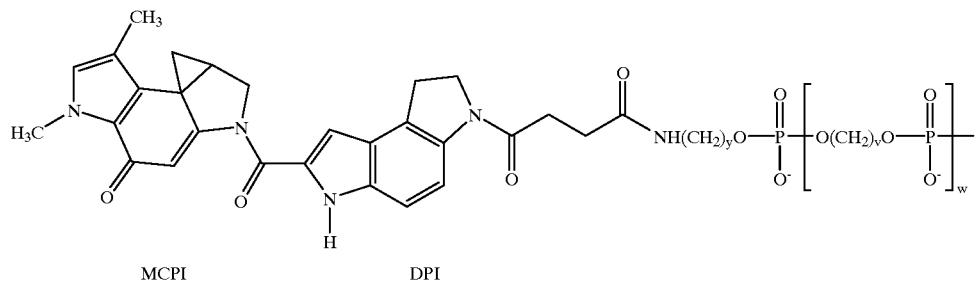

MCPI    DPI where v is an integer approximately between 1 to 4, w is an integer approximately between 3–15, and y is an integer approximately between 3 and 10.

27. A triplex in accordance with claim 26 where v is 3, w is 8 and y is 6.

28. A triplex in accordance with claim 17 where $X_2$ is O.

29. A triplex in accordance with claim 17 where $X_2$ is NH.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: double
      (D) TOPOLOGY: linear (xi) SEQUENCE DESCRIPTION: SEQ ID NO:1:

AGAAGGAGAG AGGAGAGGAA AGAGGAGACA A          31

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1
      (D) OTHER INFORMATION: /note= "6-amino-n-hexyl tail at 5'
          end"

(ix) FEATURE:
      (A) NAME/KEY: misc_feature
      (B) LOCATION: 21
      (D) OTHER INFORMATION: /note= "6-hydroxyl-n-hexyl tail at
          3' end"

(xi) SEQUENCE DESCRIPTION: SEQ ID NO:2:

AGGAGAAAGG AGAGGAGAGA G          21

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1
      (D) OTHER INFORMATION: /note= "6-amino-n-hexyl tail at 5'
          end"

(ix) FEATURE:
      (A) NAME/KEY: misc_feature
      (B) LOCATION: 21
      (D) OTHER INFORMATION: /note= "6-hydroxyl-n-hexyl tail at
          3' end"

(ix) FEATURE:
      (A) NAME/KEY: modified_base
      (B) LOCATION: 1..21
      (D) OTHER INFORMATION: /note= "all guanine nucleotides (G)
          were replaced with
          6-amino-1H-pyrazolo[3,4-d]pyrimidine-4(5H)-one
          (ppG) analog"

(xi) SEQUENCE DESCRIPTION: SEQ ID NO:3:

AGGAGAAAGG AGAGGAGAGA G          21

(2) INFORMATION FOR SEQ ID NO:4:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (xi) SEQUENCE DESCRIPTION: SEQ ID NO:4:

CTACAGGCTT AAGCCTGGAA GAGAAGGAGA GAGGAGAGGA AAGAGGAGAC AAAGTGTACA        60

TTTAC                                                                   65

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note=
            "chlorambucil-6-amino-n-hexyl tail at 5' end"

(ix) FEATURE:
        (A) NAME/KEY: misc_feature
        (B) LOCATION: 21
        (D) OTHER INFORMATION: /note= "6-hydroxy-n-hexyl tail at
            3' end"

(xi) SEQUENCE DESCRIPTION: SEQ ID NO:5:

AGGAGAAAGG AGAGGAGAGA G                                                  21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note=
            "chlorambucil-6-amino-n-hexyl tail at 5' end"

(ix) FEATURE:
        (A) NAME/KEY: misc_feature
        (B) LOCATION: 21
        (D) OTHER INFORMATION: /note= "6-hydroxy-n-hexyl tail at
            3' end"

(ix) FEATURE:
        (A) NAME/KEY: modified_base
        (B) LOCATION: 1..21
        (D) OTHER INFORMATION: /note= "all guanine bases (G) have
            been replaced with
            6-amino-1H-pyrazolo[3,4-d]pyrimidine-4(5H)-one
            (ppG) analog"

(xi) SEQUENCE DESCRIPTION: SEQ ID NO:6:

AGGAGAAAGG AGAGGAGAGA G                                                  21

(2) INFORMATION FOR SEQ ID NO:7:

(i) SEQUENCE CHARACTERISTICS:
        (A) LENGTH: 24 base pairs
        (B) TYPE: nucleic acid

```
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "5' end tail described in
            Formula 12 of the application"

(ix) FEATURE:
        (A) NAME/KEY: misc_feature
        (B) LOCATION: 24
        (D) OTHER INFORMATION: /note= "6-hydroxy-n-hexyl tail at
            3' end"

(xi) SEQUENCE DESCRIPTION: SEQ ID NO:7:

AGGAGAGGAG AGAGGAAGAG AAGG                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "5' end tail described in
            Formula 12 of the application"

(ix) FEATURE:
        (A) NAME/KEY: misc_feature
        (B) LOCATION: 24
        (D) OTHER INFORMATION: /note= "6-hydroxy-n-hexyl tail at
            3' end"

(ix) FEATURE:
        (A) NAME/KEY: modified_base
        (B) LOCATION: 1..24
        (D) OTHER INFORMATION: /note= "all guanine nucleotides (G)
            have been replaced with
            6-amino-1H-pyrazolo[3,4-d]pyrimidine-4(5H)-one
            (ppG) analog"

(xi) SEQUENCE DESCRIPTION: SEQ ID NO:8:

AGGAGAGGAG AGAGGAAGAG AAGG                                              24
```